(12) United States Patent
Jast et al.

(10) Patent No.: US 10,675,018 B2
(45) Date of Patent: Jun. 9, 2020

(54) NEEDLE GUIDE INSTRUMENT WITH TRANSVERSE SUTURE CAPTURE FEATURE

(71) Applicant: ETHICON LLC, Guaynabo, PR (US)

(72) Inventors: John A. Jast, Morrow, OH (US); Kevin A. Larson, South Lebanon, OH (US); John V. Hunt, Cincinnati, OH (US); Michael A. Jacobs, Villa Hills, KY (US); Gregory J. Bakos, Mason, OH (US); Jason L. Harris, Lebanon, OH (US); Frederick E. Shelton, IV, Hillsboro, OH (US); Jerome R. Morgan, Cincinnati, OH (US); Christopher J. Hess, Blue Ash, OH (US)

(73) Assignee: Ethicon LLC, Guaynabo, PR (US)

( * ) Notice: Subject to any disclaimer, the term of this patent is extended or adjusted under 35 U.S.C. 154(b) by 253 days.

(21) Appl. No.: 15/637,690

(22) Filed: Jun. 29, 2017

(65) Prior Publication Data
US 2019/0000443 A1 Jan. 3, 2019

(51) Int. Cl.
*A61B 17/04* (2006.01)
*A61B 17/34* (2006.01)
(Continued)

(52) U.S. Cl.
CPC ...... *A61B 17/0485* (2013.01); *A61B 17/0469* (2013.01); *A61B 17/0482* (2013.01);
(Continued)

(58) Field of Classification Search
CPC . A61B 17/04; A61B 17/0482; A61B 17/0483; A61B 17/0493; A61B 17/34;
(Continued)

(56) References Cited

U.S. PATENT DOCUMENTS 5,792,135 A 8/1998 Madhani et al.
5,817,084 A 10/1998 Jensen
(Continued)

OTHER PUBLICATIONS

U.S. Appl. No. 15/637,683, filed Jun. 29, 2017.
(Continued)

*Primary Examiner* — Melanie R Tyson
(74) *Attorney, Agent, or Firm* — Frost Brown Todd LLC

(57) ABSTRACT

A trocar assembly includes a cannula assembly, an obturator assembly, and a catch arm. The cannula assembly has a housing, a cannula, and a working channel defining a longitudinal axis from a proximal opening to a distal opening. The obturator assembly includes a proximal head, a distal tip, and a shaft extending therebetween. The catch arm is selectively moveable from a retracted position to a first and second deployed positions and is configured to releasably capture a suture thread. In the retracted position, the catch arm is positioned radially inward from the first deployed position. In the first deployed position, the catch arm is positioned radially outward from the retracted position. In addition, the catch arm is configured to be moved a predetermined distance from the first deployed position to the second deployed position and release the captured suture thread therefrom.

20 Claims, 22 Drawing Sheets

(51) Int. Cl.
*A61B 17/06* (2006.01)
*A61B 17/00* (2006.01)

(52) U.S. Cl.
CPC .... *A61B 17/06066* (2013.01); *A61B 17/3417* (2013.01); *A61B 17/3421* (2013.01); *A61B 17/0401* (2013.01); *A61B 2017/00637* (2013.01); *A61B 2017/0409* (2013.01); *A61B 2017/3454* (2013.01); *A61B 2017/3484* (2013.01)

(58) Field of Classification Search
CPC ............ A61B 17/3403; A61B 17/3417; A61B 17/3419; A61B 17/3421; A61B 17/3423; A61B 17/3462; A61B 17/3474; A61B 2017/00637; A61B 2017/3445; A61B 2017/3449; A61B 2017/3466; A61B 2017/3419
See application file for complete search history.

(56) References Cited

U.S. PATENT DOCUMENTS

| | | | |
|---|---|---|---|
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,160,309 | B2 | 1/2007 | Voss |
| 7,524,320 | B2 | 4/2009 | Tierney et al. |
| 7,691,098 | B2 | 4/2010 | Wallace et al. |
| 7,806,891 | B2 | 10/2010 | Nowlin et al. |
| 7,824,419 | B2 | 11/2010 | Boraiah |
| 7,981,092 | B2 | 7/2011 | Duke |
| 8,226,553 | B2 | 7/2012 | Shelton, IV et al. |
| 8,251,900 | B2 | 8/2012 | Ortiz et al. |
| 8,479,969 | B2 | 7/2013 | Shelton, IV |
| 8,568,362 | B2 | 10/2013 | Moreno et al. |
| 8,573,461 | B2 | 11/2013 | Shelton, IV et al. |
| 8,573,465 | B2 | 11/2013 | Shelton, IV |
| 8,579,807 | B2 | 11/2013 | Moreno et al. |
| 8,602,288 | B2 | 12/2013 | Shelton, IV et al. |
| 8,616,431 | B2 | 12/2013 | Timm et al. |
| 8,636,686 | B2 | 1/2014 | Minnelli et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,301,759 | B2 | 4/2016 | Spivey et al. |
| 9,636,104 | B2 | 5/2017 | Mohajer-Shojaee |
| 9,668,727 | B2 | 6/2017 | Heneveld |
| 9,687,226 | B2 | 6/2017 | Hodgkinson et al. |
| 9,700,303 | B2 | 7/2017 | Prior et al. |
| 9,962,145 | B2 | 5/2018 | Madsen et al. |
| 2008/0200950 | A1 | 8/2008 | Wohlert |
| 2011/0082473 | A1 | 4/2011 | Smith |
| 2013/0310856 | A1* | 11/2013 | Sherts ................ A61B 17/0482 606/148 |
| 2015/0038793 | A1* | 2/2015 | Prior .................... A61M 5/329 600/204 |
| 2015/0038800 | A1* | 2/2015 | Prior .................. A61B 17/0482 600/235 |
| 2017/0281154 | A1 | 10/2017 | Hess et al. |

OTHER PUBLICATIONS

U.S. Appl. No. 15/637,688, filed Jun. 29 2017.
U.S. Appl. No. 15/637,696, filed Jun. 29, 2017.
U.S. Appl. No. 15/637,702, filed Jun. 29, 2017.
U.S. Appl. No. 15/637,707, filed Jun. 29, 2017.
U.S. Appl. No. 15/637,712, filed Jun. 29, 2017.
U.S. Appl. No. 15/637,735, filed Jun. 29, 2017.
U.S. Appl. No. 15/637,778, filed Jun. 29, 2017.
European Search Report, Extended, and Written Opinion dated Oct. 30, 2018 for Application No. EP 18180437.8, 6 pgs.
International Search Report and Written Opinion dated Aug. 23, 2018 for Application No. PCT/IB2018/054520, 13 pgs.

* cited by examiner

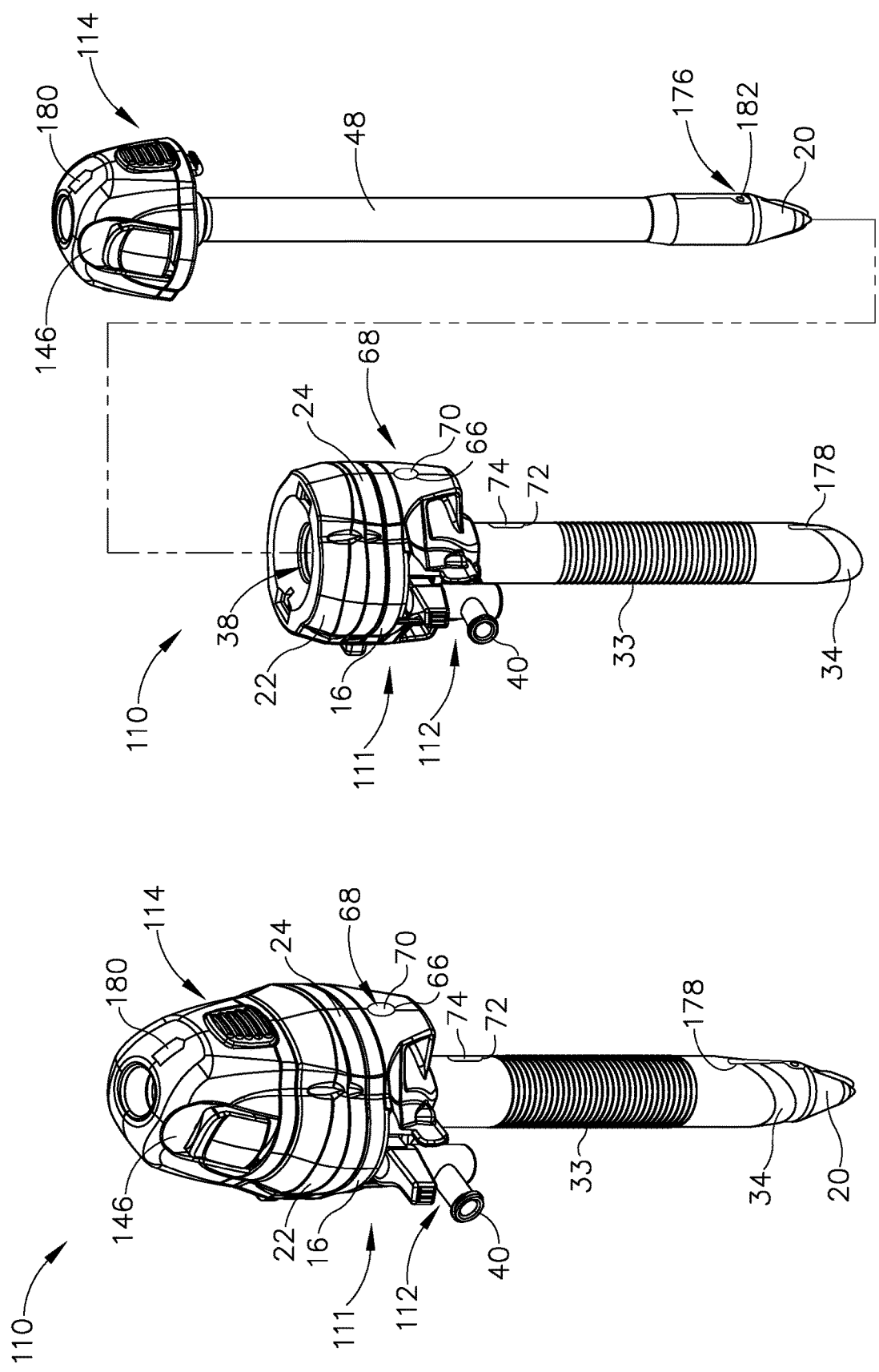

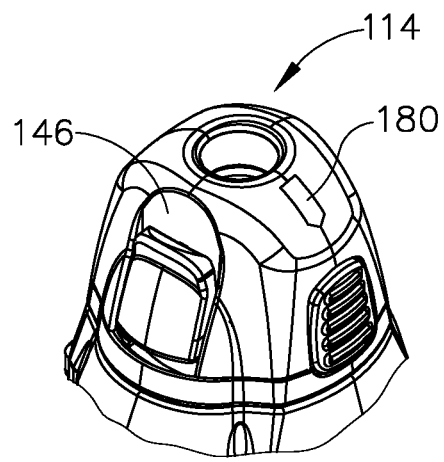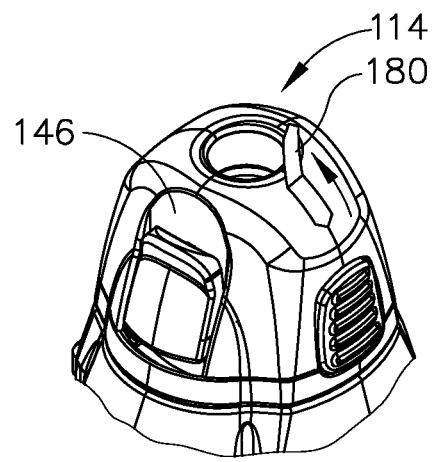
Fig.7A  Fig.7B
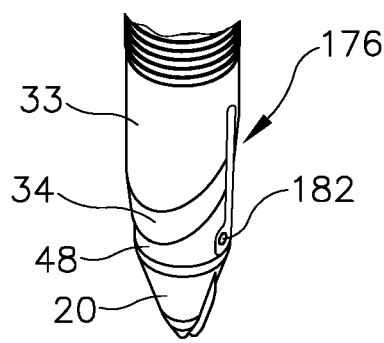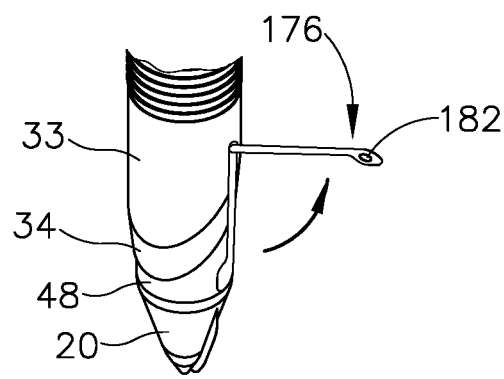
Fig.8A  Fig.8B

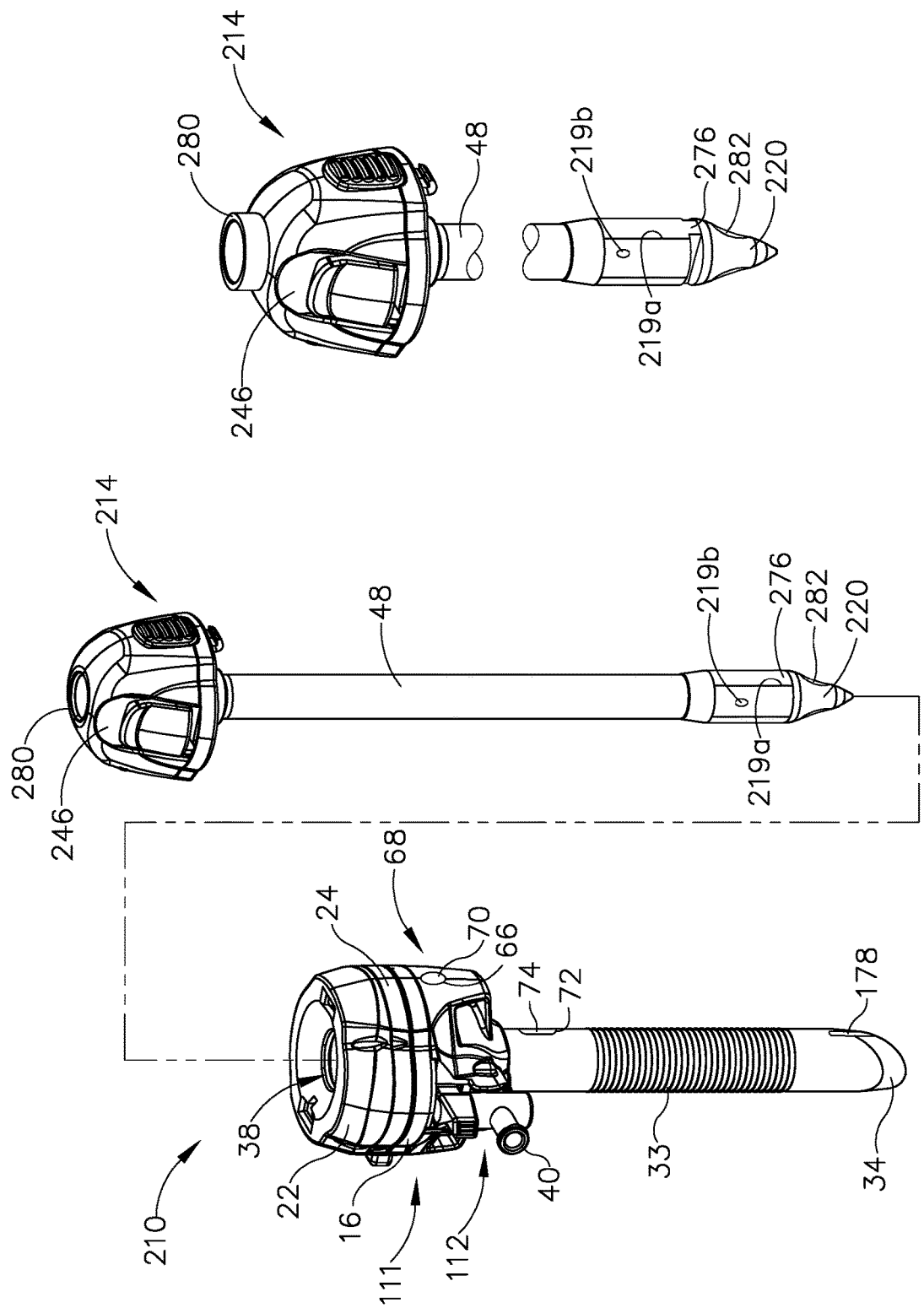

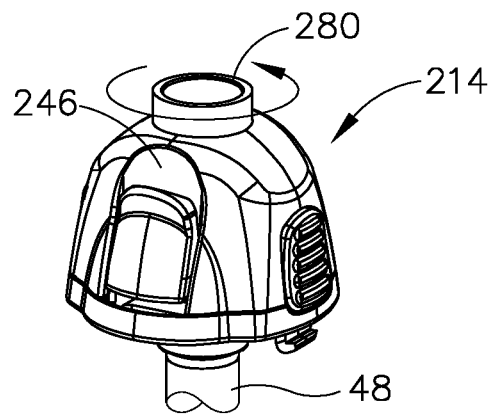
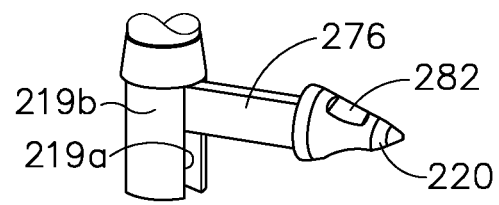
Fig.10B
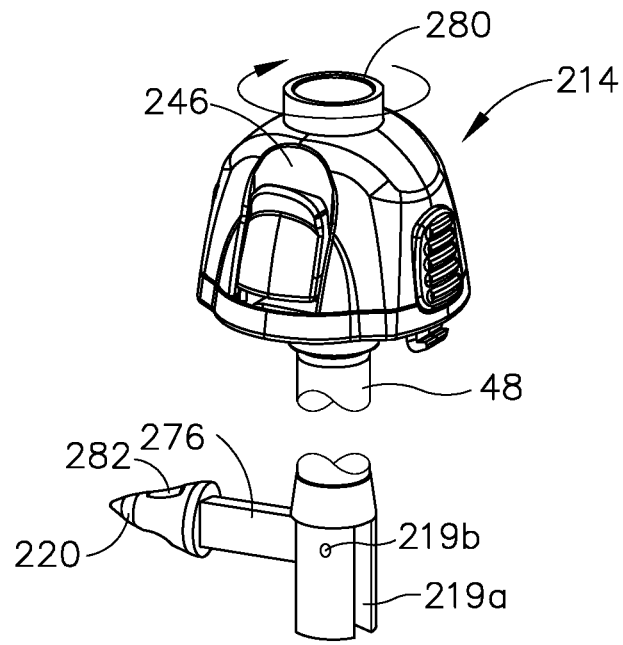
Fig.10C

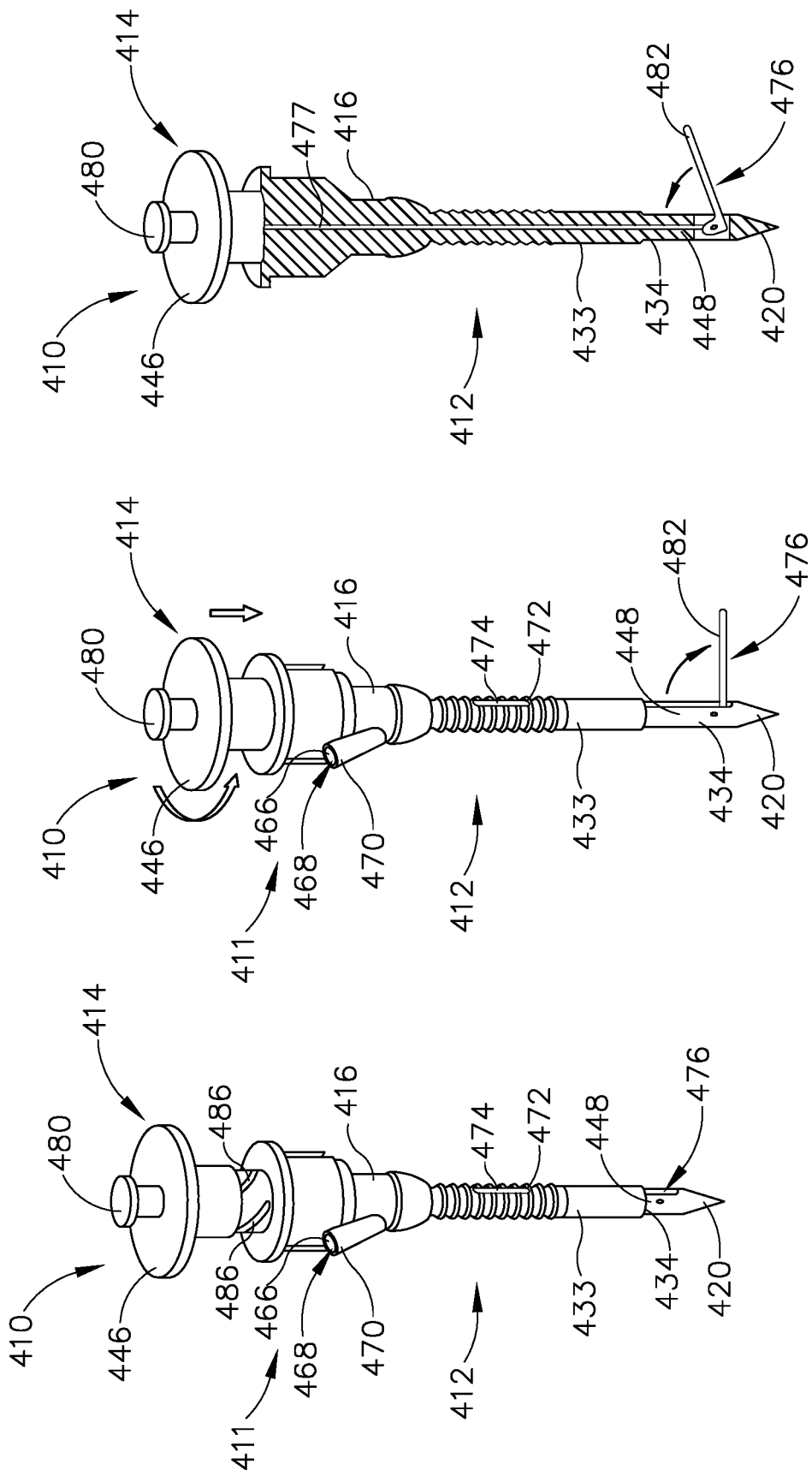

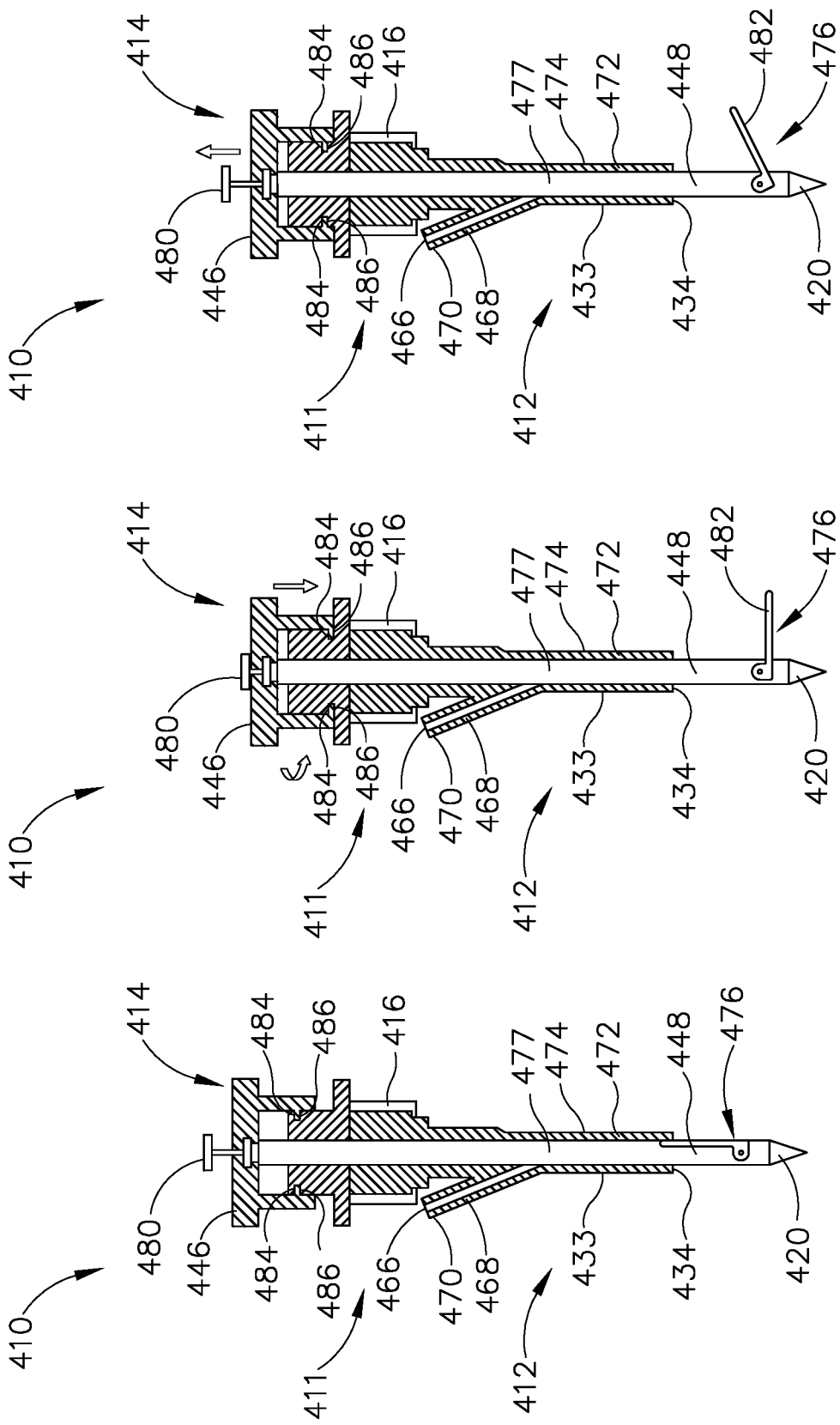

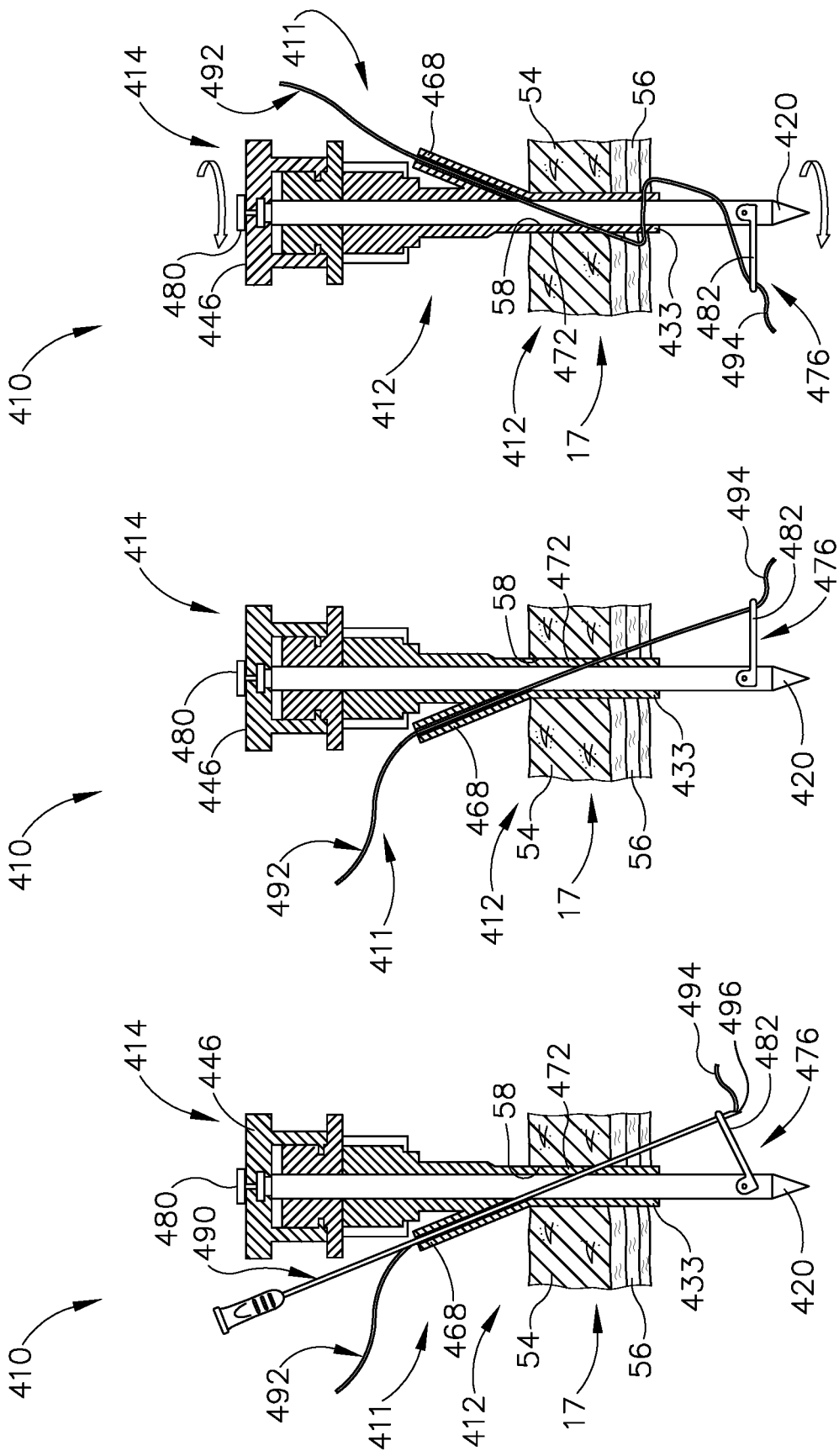

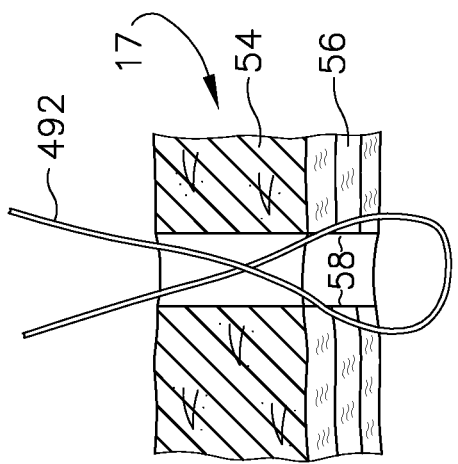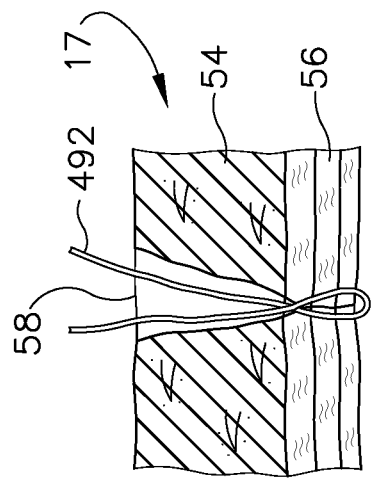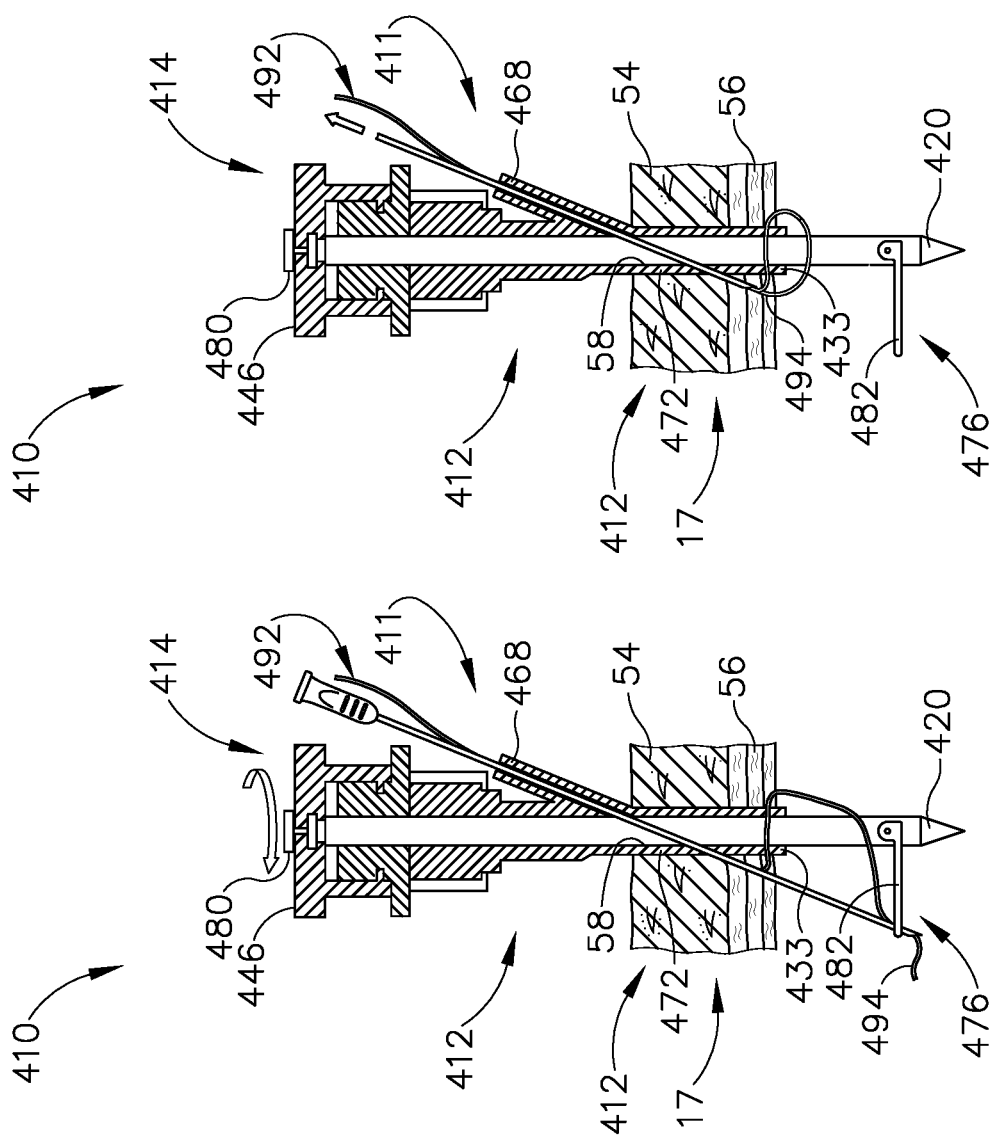

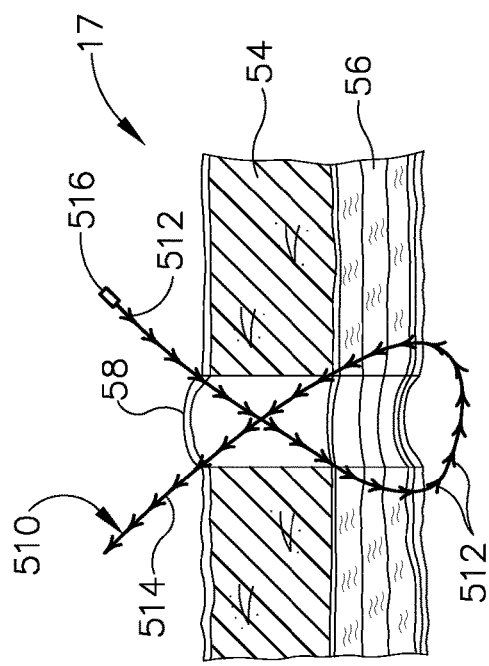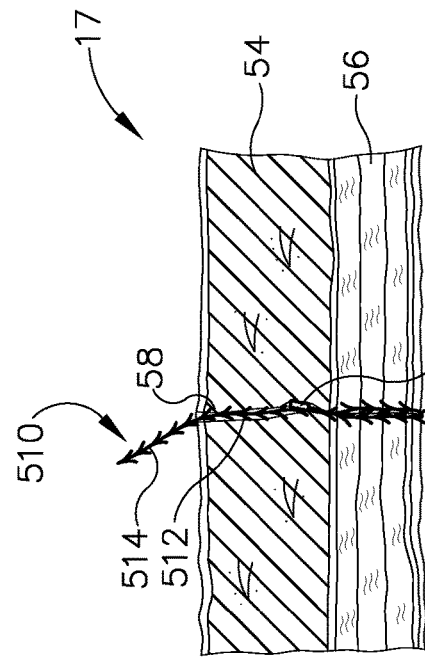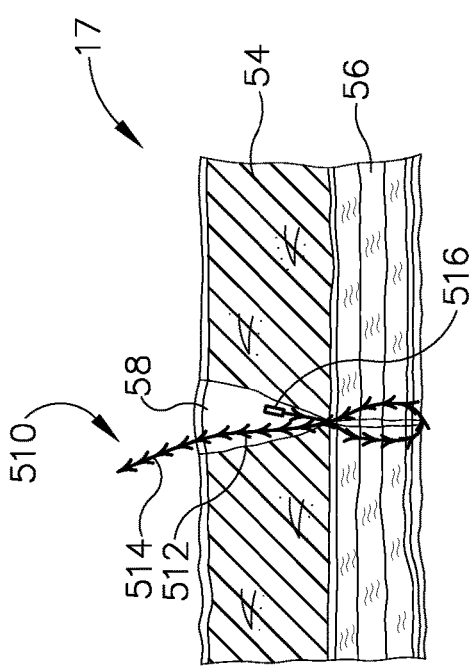

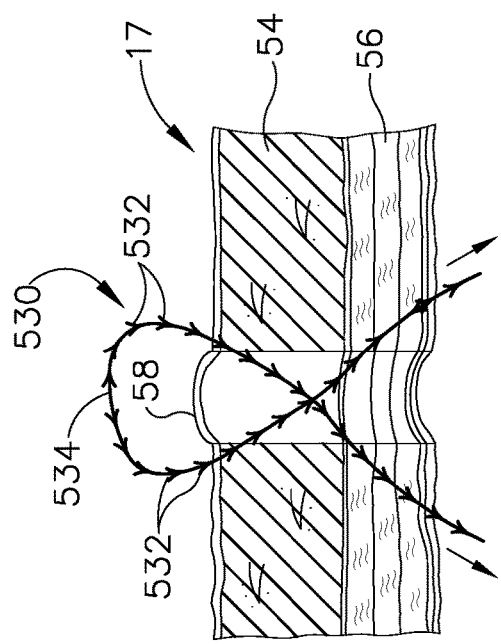
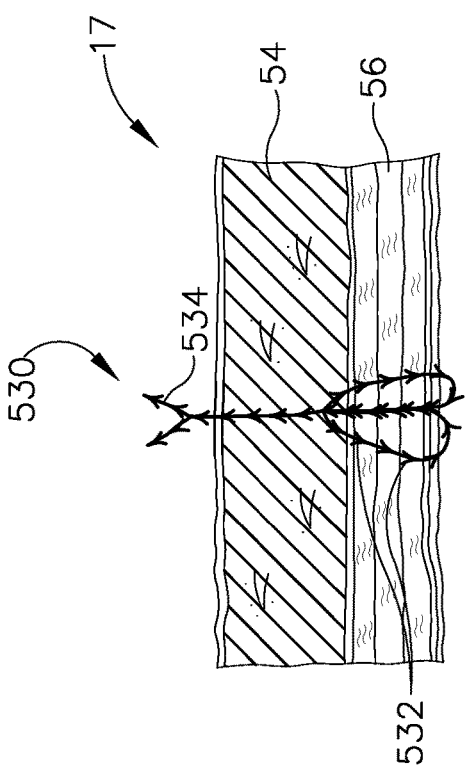
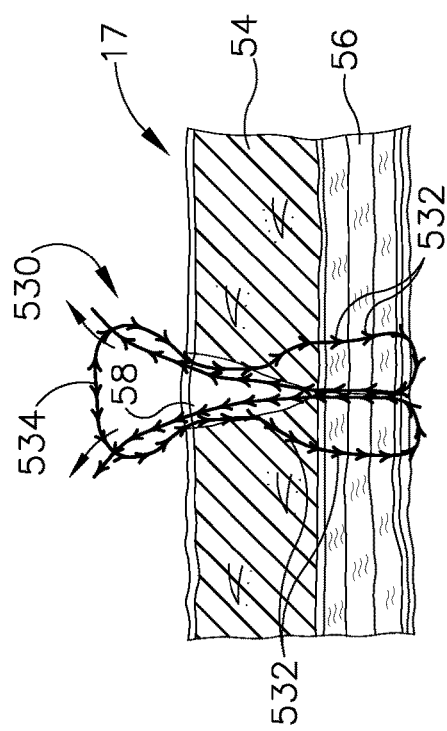
Fig.22A
Fig.22B
Fig.22C

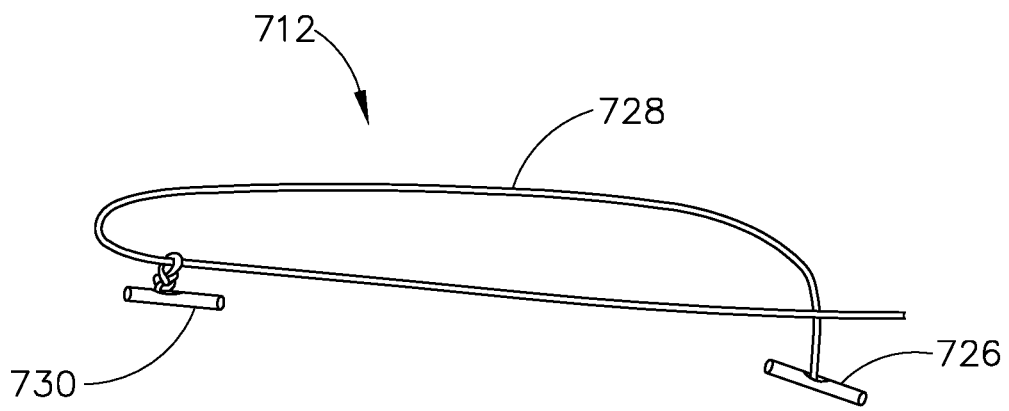
Fig.25
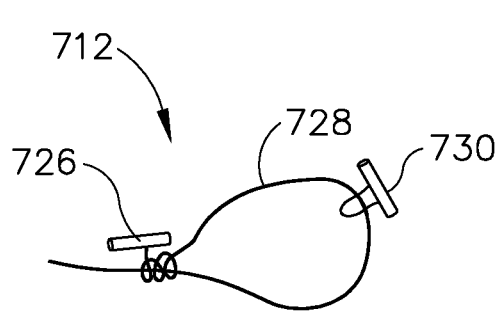  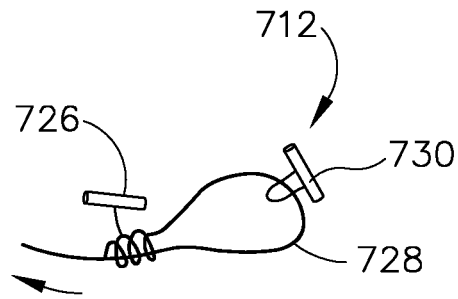
Fig.26A    Fig.26B
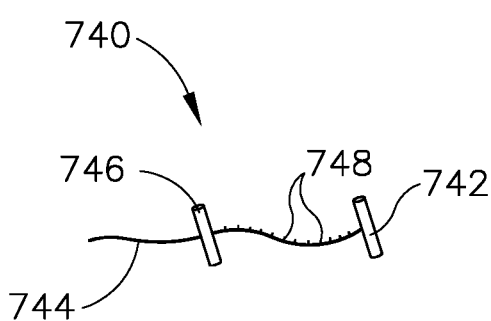  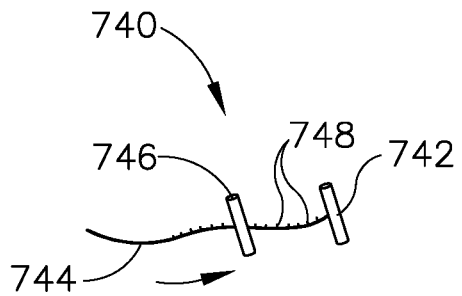
Fig.27A    Fig.27B

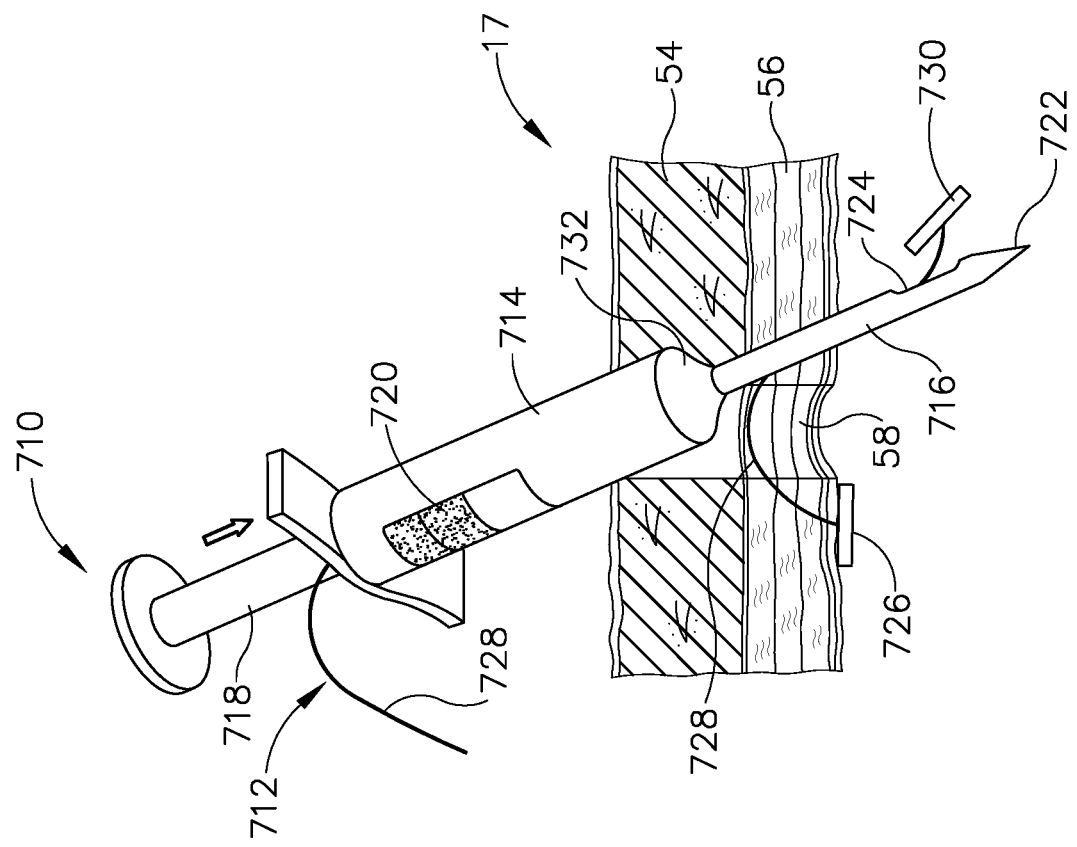
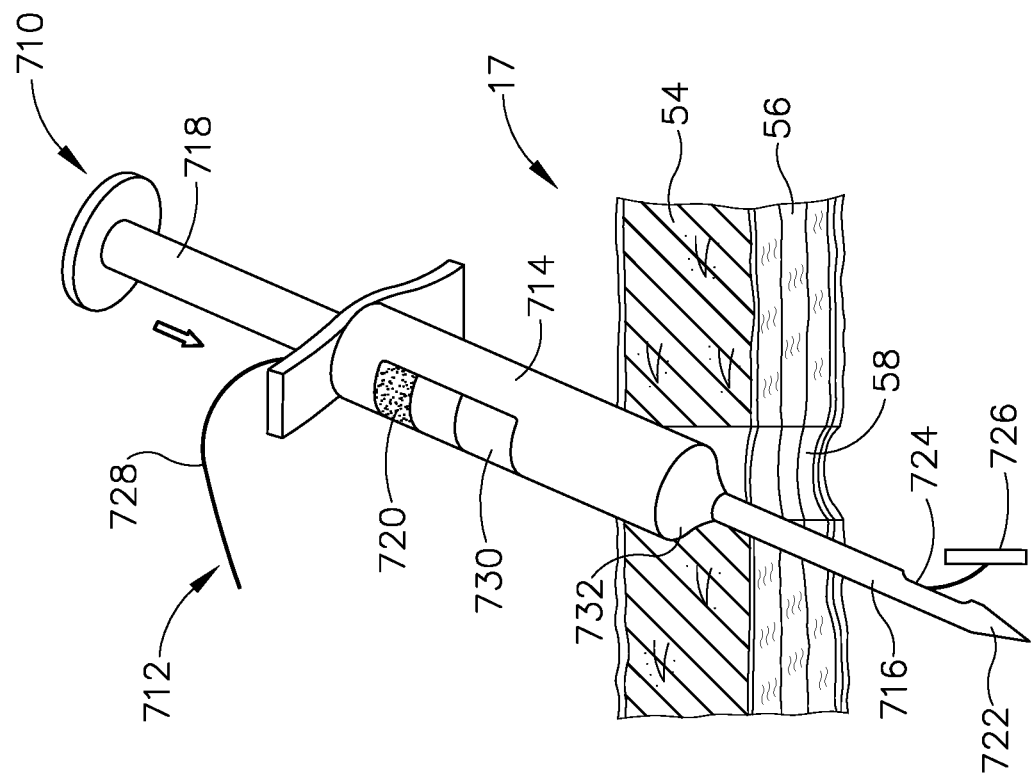

NEEDLE GUIDE INSTRUMENT WITH TRANSVERSE SUTURE CAPTURE FEATURE

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Merely exemplary trocar assemblies, components thereof, and other varieties of wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015; issued as U.S. Pat. No. 9,700,303 on Jul. 11, 2017; and U.S. Pat. Pub. No. 2015/0094741, entitled "Wound Closure Device including Mesh Barrier." Published on Apr. 2, 2015, issued as U.S. Pat. No. 9,687,226 on Jun. 27, 2017. The disclosure of each of the above-cited U.S. patents and Publications is incorporated by reference herein.

Surgical instruments for use with such trocars may have a distal end effector for engaging tissue through the trocar cannula in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including trocar assemblies and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5 depicts a perspective view of a first suturing trocar assembly having a cannula assembly and an obturator assembly with a first catch arm for releasably capturing a suture thread;

FIG. 6 depicts a partially exploded perspective view of the suturing trocar assembly of FIG. 5;

FIG. 7A depicts an enlarged perspective view of a proximal end portion of the suturing trocar assembly of FIG. 5 with an actuator in an unactuated position for extending the catch arm from a retracted position to a deployed position;

FIG. 7B depicts the enlarged perspective view of the proximal end portion of the suturing trocar assembly similar to FIG. 7A, but with the actuator manipulated to an actuated position;

FIG. 8A depicts an enlarged perspective view of a distal end portion of the suturing trocar assembly of FIG. 5 with the catch arm in the retracted position;

FIG. 8B depicts the enlarged perspective view of the distal end portion of the suturing trocar assembly similar to FIG. 8A, but with the catch arm in the deployed position;

FIG. 9 depicts a partially exploded perspective view of a second suturing trocar assembly having a cannula assembly and an obturator assembly with a second catch arm for releasably capturing a suture thread;

FIG. 10A depicts a perspective view of the suturing trocar assembly of FIG. 9 with the catch arm in a retracted position;

FIG. 10B depicts the perspective view of the suturing trocar assembly similar to FIG. 10A, but with the catch arm in a deployed position;

FIG. 10C depicts the perspective view of the suturing trocar assembly similar to FIG. 10B, but with the catch arm in another deployed position;

FIG. 13A depicts a perspective view of a fourth suturing trocar assembly having a cannula assembly with a fourth catch arm for releasably capturing a suture thread in a retracted state;

FIG. 13B depicts the perspective view of the suturing trocar assembly similar to FIG. 13A, but with the catch arm extended from the retracted position to a deployed position;

FIG. 13C depicts a cross-sectional perspective view of the suturing trocar assembly similar to FIG. 13B, but with the catch arm being returned from the deployed position to the retracted position;

FIG. 14A depicts a cross-sectional view of the suturing trocar assembly of FIG. 13A taken along a longitudinal centerline thereof;

FIG. 14B depicts a cross-sectional view of the suturing trocar assembly of FIG. 13B taken along the longitudinal centerline thereof;

FIG. 14C depicts a cross-sectional view of the suturing trocar assembly of FIG. 13C taken along the longitudinal centerline thereof;

FIG. 15A depicts a cross-sectional view of the suturing trocar assembly of FIG. 13A taken along a longitudinal centerline thereof positioned within a tissue opening and receiving a needle with a suture thread;

FIG. 15B depicts the cross-sectional view of the suturing trocar assembly similar to FIG. 15A, but showing the needle removed therefrom and the suture thread releasably captured by the catch arm in a catch deployed position;

FIG. 15C depicts the cross-sectional view of the suturing trocar assembly similar to FIG. 15B, but with the catch arm and the suture thread rotated to a release deployed position;

FIG. 15D depicts the cross-sectional view of the suturing trocar assembly similar to FIG. 15C, but with the needle again received within the suturing trocar assembly and reattaching to the suture thread;

FIG. 15E depicts the cross-sectional view of the suturing trocar assembly similar to FIG. 15D, but with the needle and the suture thread being withdrawn from the suturing trocar assembly;

FIG. 15F depicts a cross-sectional view similar to FIG. 15E, but with the suturing trocar assembly removed from the tissue opening such that the suture thread remains therein;

FIG. 15G depicts a cross-sectional view similar to FIG. 15F, but with the suture thread closing the tissue opening to form a suture;

FIG. 19A depicts a cross-sectional view of a tissue having received the unidirectional barbed suture of FIG. 16 within a tissue opening;

FIG. 19B depicts the cross-sectional view of the tissue and the unidirectional barbed suture similar to FIG. 19A, but showing the unidirectional barbed suture closing the tissue opening;

FIG. 19C depicts the cross-sectional view of the tissue and the unidirectional barbed suture similar to FIG. 19B, but showing the unidirectional barbed suture having closed the tissue opening;

FIG. 22A depicts a cross-sectional view of the tissue and the bidirectional barbed suture of FIG. 21B in an opening of the tissue;

FIG. 22B depicts the cross-sectional view of the tissue and the bidirectional barbed suture similar to FIG. 21A, but showing the bidirectional barbed suture closing the tissue opening;

FIG. 22C depicts the cross-sectional view of the tissue and the bidirectional barbed suture similar to FIG. 22B, but showing the bidirectional barbed suture having closed the tissue opening;

FIG. 25 depicts a perspective view of the slip pledget suture thread of FIG. 23;

FIG. 26A depicts a perspective view of the slip pledget suture thread of FIG. 25 in a looped opened configuration;

FIG. 26B depicts the perspective view of the slip pledget suture thread similar to FIG. 26A, but showing the slip pledget suture thread being closed from the looped open configuration to a looped closed configuration;

FIG. 27A depicts a perspective view of a barbed pledget suture thread in an extended opened configuration;

FIG. 27B depicts the perspective view of the barbed pledget suture thread similar to FIG. 27A, but showing the barbed pledget suture thread being closed from the extended open configuration to a contracted closed configuration;

FIG. 28A depicts a perspective sectional view of the suturing surgical instrument and the slip pledget suture thread of FIG. 23 inserted into a tissue opening of a tissue to position a pledget into a tissue portion about the tissue opening;

FIG. 28B depicts the perspective sectional view of the suturing surgical instrument and the slip pledget suture thread similar to FIG. 28A, but with another pledget inserted into another tissue portion about the tissue opening;

Figure 1:
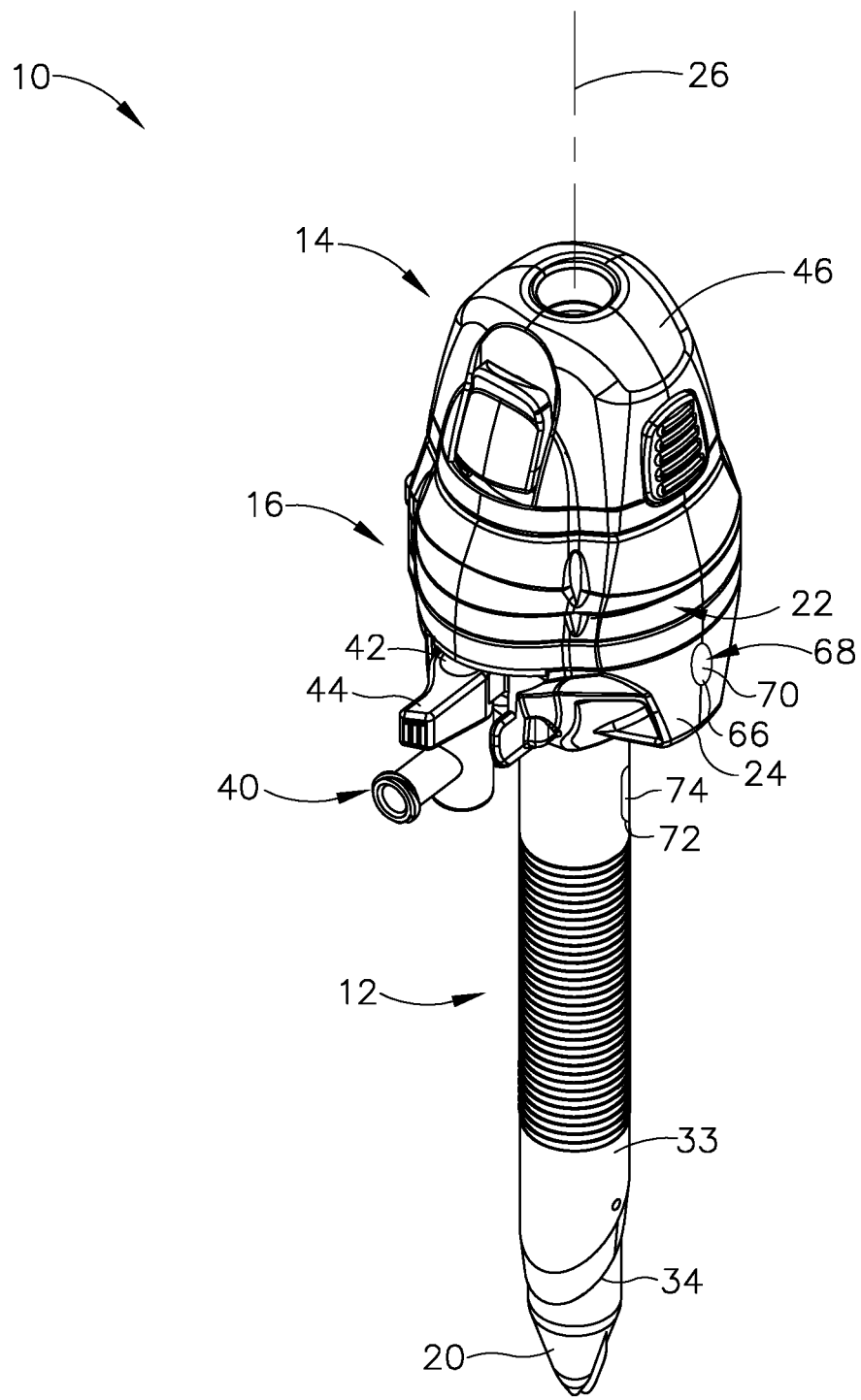
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
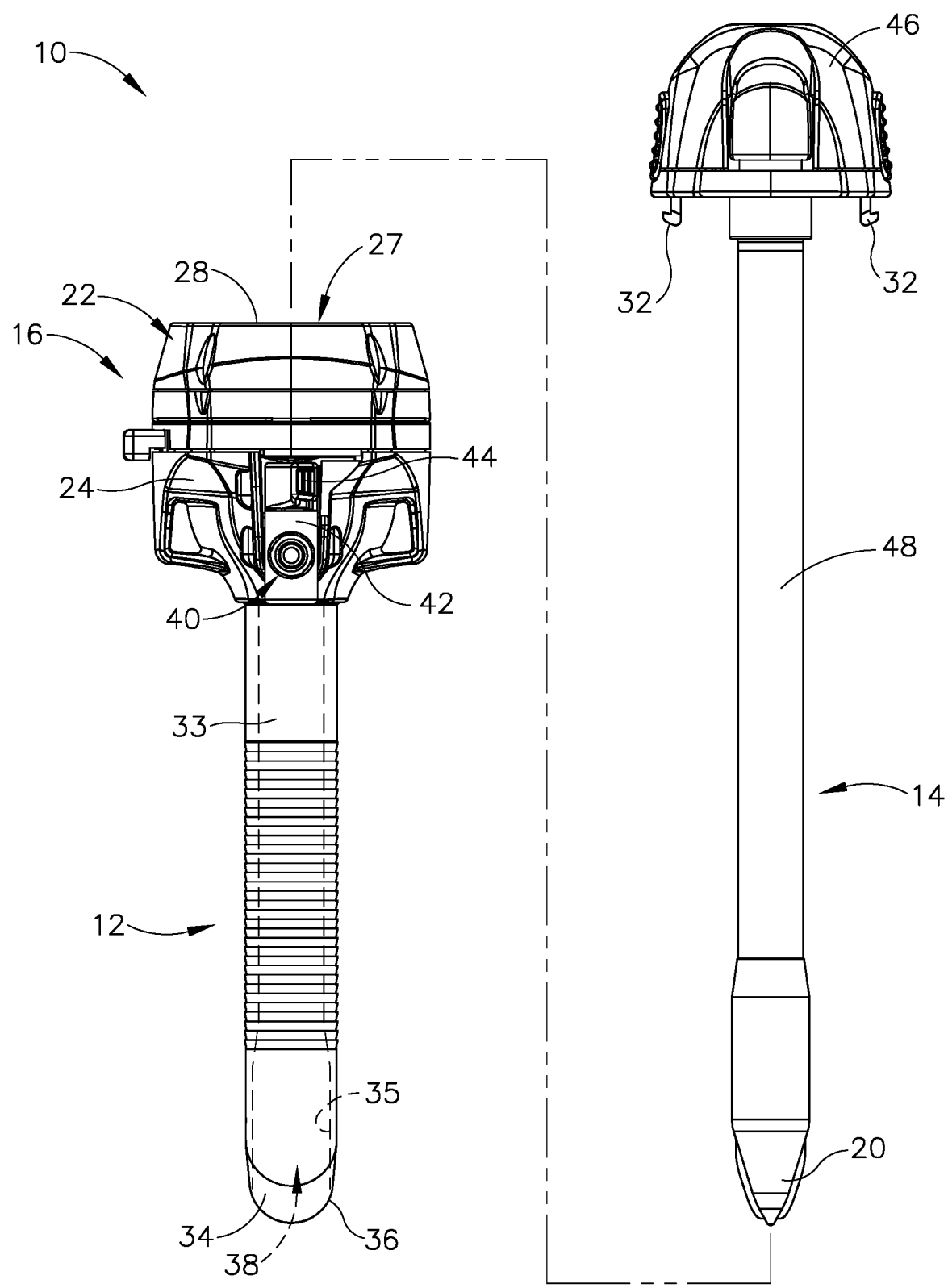
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a cannula assembly (11) having a trocar cannula (12) and a trocar obturator assembly (14). Trocar obturator assembly (14) is removably received within trocar cannula (12) through a trocar housing (16) of cannula assembly (11). As shown in FIG. 1 with trocar obturator assembly (14) positioned within trocar cannula (12), a clinician inserts trocar assembly (10) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator assembly (14) projects distally from trocar cannula (12) to penetrate tissue (17) (see FIG. 3A) for introducing a distal end portion of trocar cannula (12) into cavity (18) (see FIG. 3B). The clinician proximally withdraws trocar obturator assembly (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zeroclosure seal, such as a duckbill seal (not shown). Instrument seal (not shown) is retained with cap (22) and configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to penetrate tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
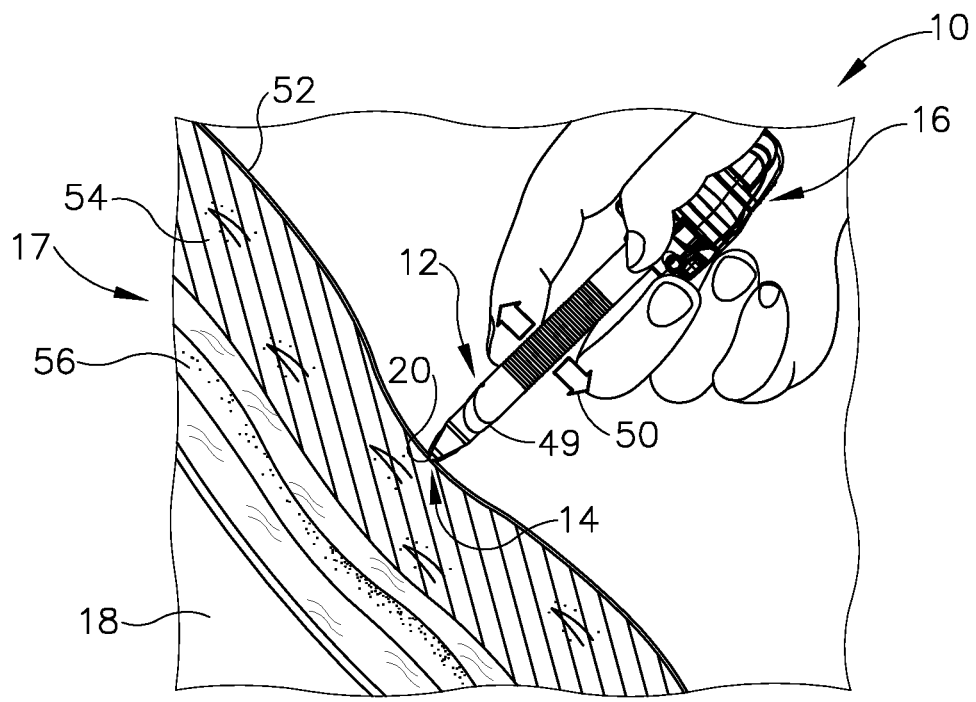
FIG. 3A depicts a sectional side view of tissue of a patient with the trocar assembly of FIG. 1 being manipulated by a clinician through the tissue.
Figure 3B:
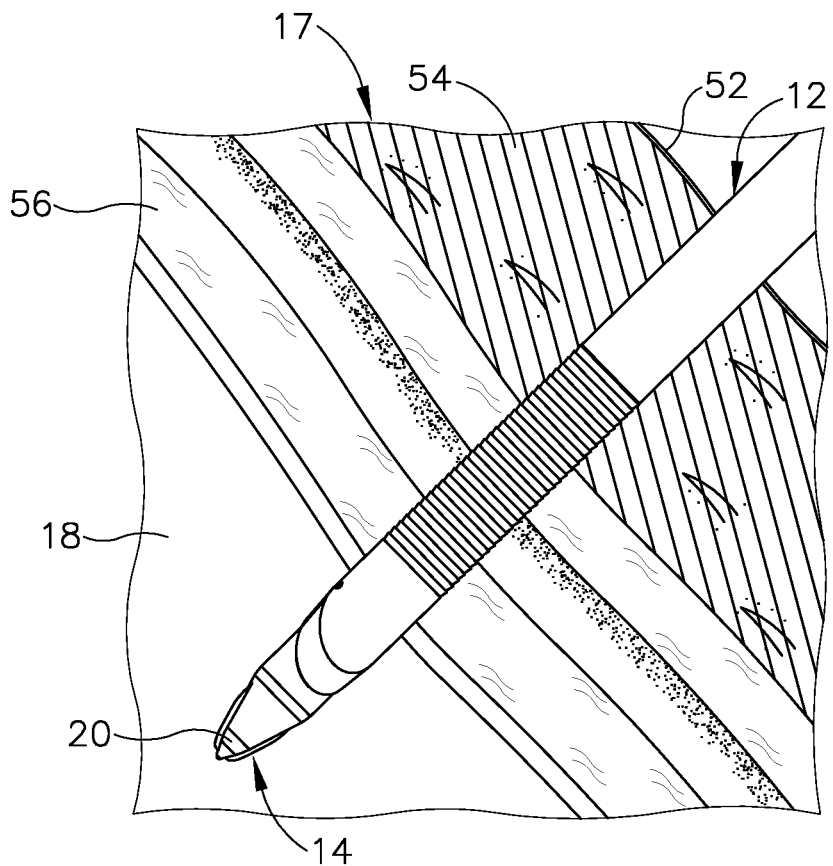
FIG. 3B depicts a sectional side view of the tissue and trocar assembly of FIG. 3A, with the trocar assembly of FIG. 1 inserted through the tissue and received within a cavity of the patient.
Figure 3C:
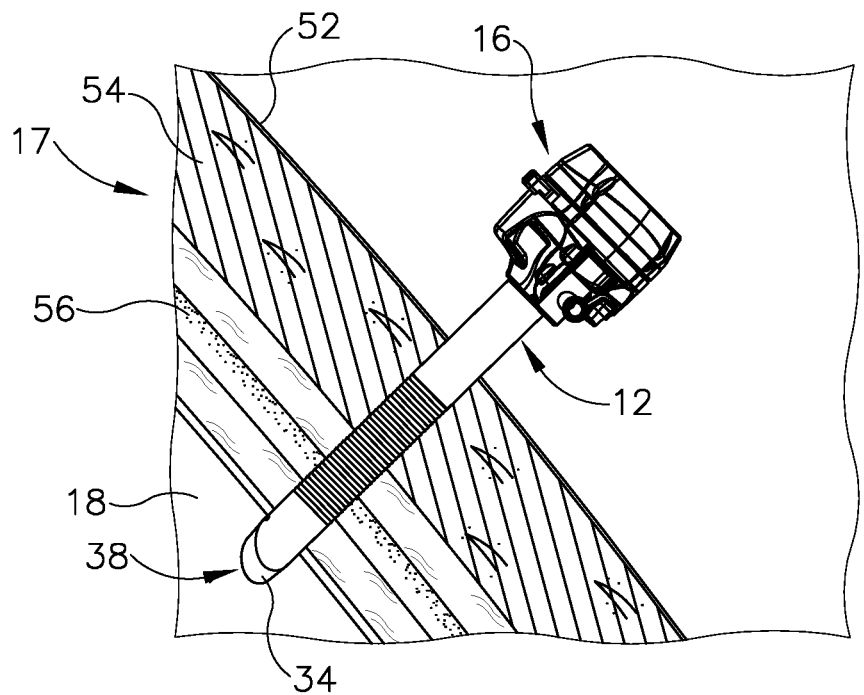
FIG. 3C depicts a sectional side view of the tissue and the trocar assembly of FIG. 3A, with the obturator withdrawn from the trocar cannula for accessing the cavity via a working channel through the trocar cannula and the trocar housing.
Figure 3D:
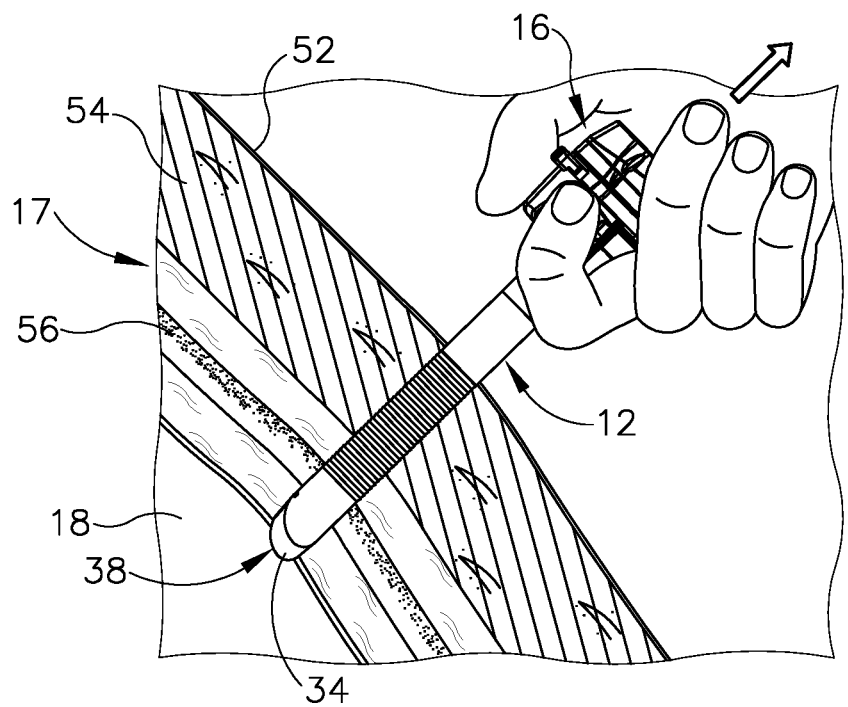
FIG. 3D depicts a sectional side view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
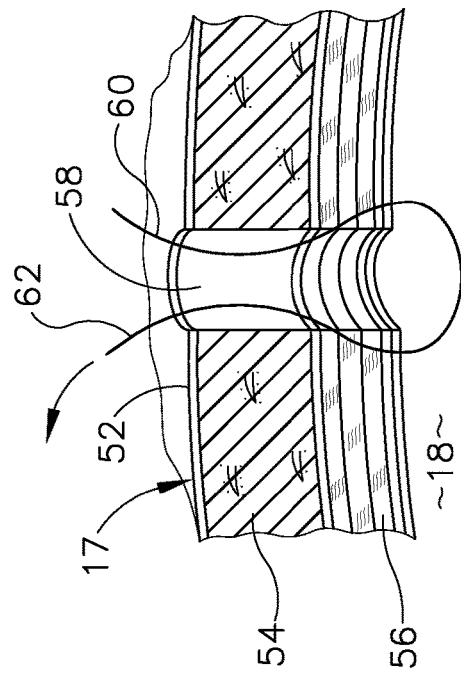
FIG. 4A depicts another sectional side view of the tissue shown in FIGS. 3A-3D following removal of the trocar assembly of FIG. 1, with an opening through the tissue and a suture thread being introduced into a portion of the tissue for suturing the opening closed.
Figure 4B:
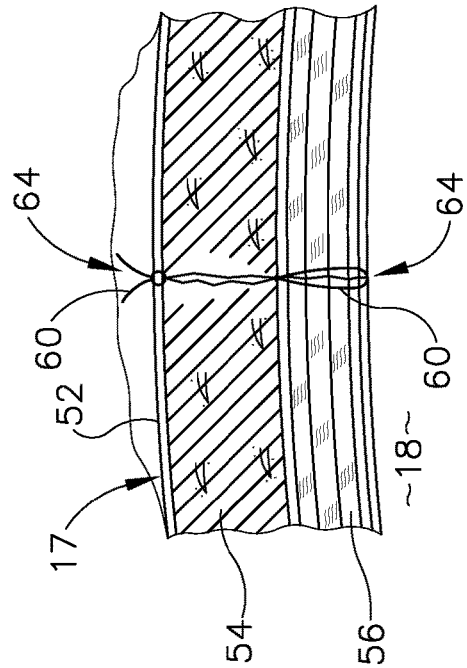
FIG. 4B depicts a sectional side view of the tissue of FIG. 4A, with the suture thread being introduced though another portion of the tissue and pulled through the tissue.
Figure 4C:
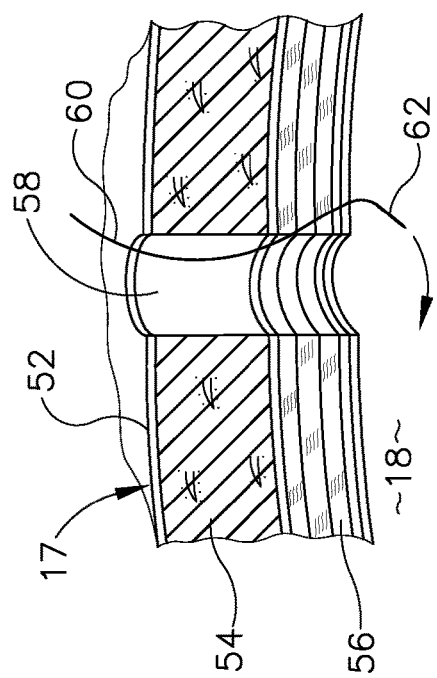
FIG. 4C depicts a sectional side view of the tissue of FIG. 4A, with the suture thread tightened and knotted for at least partially closing the opening.
Figure 4D:
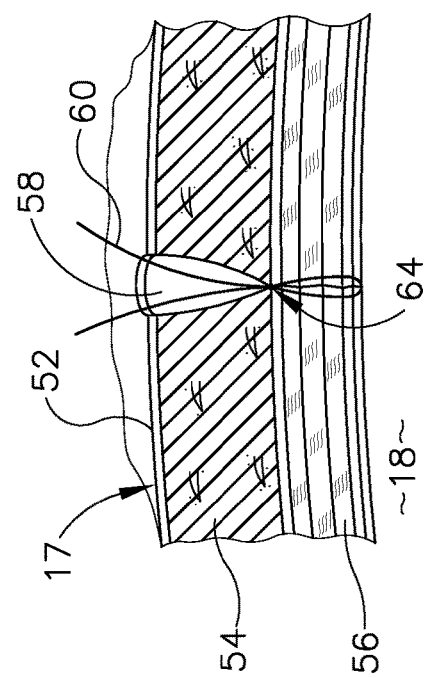
FIG. 4D depicts a sectional side view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance from tissue opening (58) in order to provide a relatively close proximity to tissue opening (58); but also at a sufficient distance to provide ample fascia (56) for anchoring suture thread (60) therein. As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed on Apr. 1, 2016, which is incorporated by reference herein in its entirety, describes an alternative trocar assembly and suturing technique. To this end, alternative trocar assemblies and suturing techniques may be used in any combination as desired by the clinician.

II. Various Suturing Trocar Assemblies with a Deployable Catch Arm

Generally, withdrawing trocar assembly (10) to reveal tissue opening (58) as shown with respect to FIGS. 1-3D may provide for sufficient space and visibility in many instances to thereby suture tissue opening (58) closed as shown in FIGS. 4A-4D. However, in some instances, it may be desirable to suture tissue opening (58) closed while trocar assembly (10) remains in tissue opening (58). To this end, trocar assembly (10) of FIGS. 1-2 has opposed openings (66) disposed in trocar housing (16) through which to suture tissue (17) while trocar assembly (10) is positioned within tissue opening (58). Openings (66) are formed in housing sidewall (24) and extend therethrough across a longitudinal axis along a channel (68). A seal (70) is disposed within channel (68) at opening (66), which serves as a proximal entrance port for a needle (490) (see FIG. 15A) to be introduced into channel (68). In the illustrated example, channel (68) extends through working channel (38) at an oblique angle with respect to the longitudinal axis such that channel (68) terminates to another opening (72) with a seal (74). Opening (72) is distal of the distal-most seal, such as the duckbill seal (not shown), and defines a suture path for needle (490) (see FIG. 15A) and suture thread (492) (see FIG. 15A) between an outside environment and a surgical site.

While such instances may provide for one or more diagnostic or therapeutic effects to the patient, the resulting suturing technique may become more complicated, difficult, or tedious in one or more aspects due to the limited space and visibility about tissue opening (58). For example, even in the event that the clinician inserts needle (490) (see FIG. 15A) with suture thread (492) (see FIG. 15A) into tissue (17), releasing suture thread (492) (see FIG. 15A), repositioning suture thread (492) (see FIG. 15A), and reattaching suture thread (492) (see FIG. 15A) to needle (490) (see FIG. 15A) for withdrawal from tissue (17) may be difficult with such limited visibility of suture thread (492) (see FIG. 15A) within the patient. The difficulty of visualizing suture thread (492) (see FIG. 15A) while suturing tissue (17) may thus result in additional suturing attempts, greater surgical time, and even an increased likelihood inadvertent tissue damage.

A suturing trocar assembly (110, 210, 310, 410, 610) with a deployable catch arm (176, 276, 376, 476, 676) as described below may thus be desirable in some instances. More particularly, catch arms (176, 276, 376, 476, 676) are configured to releasably capture suture thread (492) (see FIG. 15A) from needle (490) (see FIG. 15A) and reposition suture thread (492) (see FIG. 15A) for reattaching suture thread (492) (see FIG. 15A) for withdrawal from tissue (17) (see FIG. 15A). While direct visibility may still be helpful in such instances, catch arms (176, 276, 376, 476, 676) provide the clinician with greater predictability for placing suture thread (492) (see FIG. 15A) during suturing for enhanced patient outcomes.

The following description provides various examples of suturing trocar assemblies (110, 210, 310, 410, 610) including various deployable catch arms (176, 276, 376, 476, 676). Such catch arms (176, 276, 376, 476, 676) described below may be used with any trocar assembly described above and below and in any of the various procedures described in the various patent references cited herein. To this end, like numbers below indicated like features described above. Other suitable ways in which various trocar assemblies may be used will be apparent to those of ordinary skill in the art in view of the teachings herein.

A. First Suturing Trocar Assembly with a First Deployable Catch Arm Repositioned within a Patient Via Rotation of Trocar Obturator FIGS. 5-8B illustrate a first exemplary suturing trocar assembly (110) with a cannula assembly (111) and an obturator (114). With respect to FIGS. 5-6, obturator (114) has a distal end portion with shaft (48) distally extending to tip (20). In addition, the distal end portion of obturator (114) includes a catch arm (176) that is selectively movable from a retracted position to a deployed position. In the retracted position, catch arm (176) with the remainder of the distal end portion of obturator (114) is positioned relatively radially inward and thus configured to be inserted into the patient and removed from the patient, such as via cannula (112). In the deployed position, catch arm (176) extends relatively radially outward to align with channel (68) for receiving needle (490) (see FIG. 15A) thereagainst. Catch arm (176) in the deployed position is thereby configured to releasably capture suture thread (492) (see FIG. 15A) for suturing tissue (17) (see FIG. 15A).

Cannula assembly (111) has trocar housing (16) and cannula (112) similar to those discussed above, but, in addition, has a pair of longitudinally extending clearance channels (178) on opposing lateral sides of the distal end portion of cannula sidewall (33). Each clearance channel (178) extends through cannula sidewall (33) to beveled end (34) and aligns with catch arm (176) in respective deployed positions to provide clearance for catch arm (176) to pivot through selective movement. To this end, in the present example, one of the two clearance channels (178) receives catch arm (176) in a catch deployed position to releasably capture suture thread (492) (see FIG. 15A). Once captured, catch arm (176) returns to the retracted position and obturator (114) is rotated 180 degrees relative to cannula assembly (111) such that catch arm (176) aligns with the other clearance channel (178). Catch arm (176) is then extended to a release deployed position such that needle (490) (see FIG. 15A) reattaches with suture thread (492) (see FIG. 15A) to be withdrawn via another channel (68) through tissue (17) (see FIG. 15A) as generally discussed below in use with respect to FIGS. 15A-15D.

FIGS. 7A and 8A show catch arm (176) in the retracted position in greater detail. A handle head (146) includes an actuator (180) operatively connected to catch arm (176) and configured to direct movement of catch arm (176). While not shown herein, actuator (180) is connected to catch arm (176) by a cable (not shown) for moving actuator (180). Of course, alternative mechanisms for operatively connecting actuator (180) to catch arm (176) will be appreciated by those of ordinary skill in the art. Actuator (180) in the unactuated position causes catch arm (176) to remain in the retracted position. In the present example, cannula sidewall (33) has an outer surface that defines a generally circular profile that is transverse to the longitudinal axis along which cannula (112) extends. Catch arm (176) in the retracted position is generally parallel with the longitudinal axis and within this transverse circular profile in order to inhibit catch arm (176) from engaging, or even catching, on tissue (17) (see FIG. 15A) and/or cannula (112) upon insertion. As the term "generally within" is used herein, catch arm (176) may also overlap with the transverse circular profile of cannula wall (33) and be considered generally within the transverse circular profile. In other words, catch arm (176) is at least generally flush with the outer surface of cannula sidewall (33), but may also be positioned radially inward of the outer surface of cannula sidewall (33).

Selectively manipulating actuator (180) in a proximal direction causes catch arm (176) to proximally pivot to the deployed position shown in FIGS. 7B and 8B. In the deployed position, catch arm (176) extends radially outward from shaft (48). More particularly, in the present example, catch arm (176) extends transversely relative to the longitudinal axis and radially outward to align with channel (68). Catch arm (176) further includes a catch hole (182) that extends transversely therethrough and aligns with channel (68) so that needle (490) (see FIG. 15A) may be simultaneously received within channel (68) and catch hole (182) in use. Catch arm (176) is configured to releasably capture suture thread (492) (see FIG. 15A) within catch hole (182) for suturing tissue (17) (see FIG. 15A) as described below in greater detail.

B. Second Suturing Trocar Assembly with a Second Deployable Catch Arm Repositioned within a Patient Via Pivoting Second Deployable Catch Arm FIGS. 9-10C illustrate a second exemplary suturing trocar assembly (210) with cannula assembly (111) discussed above and an obturator (214). With respect to FIG. 9, obturator (214) has a distal end portion with shaft (48) distally extending to a forked portion including a longitudinally and transversely extending slot (219a). The forked portion of obturator (114) receives a catch arm (276) pivotally mounted therein to be selectively movable from a retracted position to a deployed position. From a pivotal mounting (219b), catch arm (276) extends to a tip (220) configured to pierce tissue similar to those discussed above. Tip (220) is thus positioned on a distal end of catch arm (276) in the present example. In the retracted position, catch arm (176) with the remainder of the distal end portion of obturator (114) is positioned relatively radially inward and thus configured to be inserted into the patient and removed from the patient, such as via cannula (112). In the deployed position, catch arm (276) with tip (220) extends relatively radially outward to align tip (220) with channel (68) for receiving needle (490) (see FIG. 15A) thereagainst. Catch arm (276) in the deployed position is thereby configured to releasably capture suture thread (492) (see FIG. 15A) for suturing tissue (17) (see FIG. 15A).

Cannula assembly (111) has clearance channel (178) configured to receive catch arm (276) in a catch deployed position to releasably capture suture thread (492) (see FIG. 15A). Once captured, catch arm (276) pivots 180 degrees through the retracted position to a release deployed position transversely opposite from the catch deployed position such that catch arm (276) aligns with the other clearance channel (178). Catch arm (276) in the release deployed position is configured such that needle (490) (see FIG. 15A) reattaches with suture thread (492) (see FIG. 15A) to be withdrawn via another channel (68) through tissue (17) (see FIG. 15A) as generally discussed below in use with respect to FIGS. 15A-15D.

FIG. 10A shows catch arm (176) in the retracted position in greater detail. A handle head (246) includes a rotatable actuator (280) operatively connected to catch arm (276) and configured to direct movement of catch arm (276). Actuator (280) is resiliently depressed to proximally translate release actuator (280) for being gripped by the clinician. Actuator (280), once depressed, generally remains in the unactuated position as shown in FIG. 10A until rotated in a clockwise or a counterclockwise direction to actuated positions. In the present example, cannula sidewall (33) (see FIG. 9) has the outer surface that defines the generally circular profile that is transverse to the longitudinal axis along which cannula (112) extends. Catch arm (276) in the retracted position is generally parallel with the longitudinal axis and within this transverse circular profile. Tip (220) is configured to pierce tissue (17) (see FIG. 15A) and proximally widens in shape in order to gradually widen penetrated tissue (17) (see FIG. 15A) toward beveled end (34) upon insertion.

Selectively manipulating actuator (280) in a counterclockwise or clockwise directions as shown respectively in FIG. 10B and FIG. 10C causes catch arm (276) to pivot to the catch deployed position and the release deployed position. In each deployed position, catch arm (276) extends radially outward from shaft (48). More particularly, in the present example, catch arm (276) extends transversely relative to the longitudinal axis and radially outward to align with channel (68). Catch arm (276) further includes a catch hole (282) that extends transversely through tip (220) and aligns with channel (68) so that needle (490) (see FIG. 15A) may be simultaneously received within channel (68) and catch hole (282) in use. Catch arm (276) is configured to releasably capture suture thread (492) (see FIG. 15A) within catch hole (282) for suturing tissue (17) (see FIG. 15A) as described below in greater detail.

Figure 11:
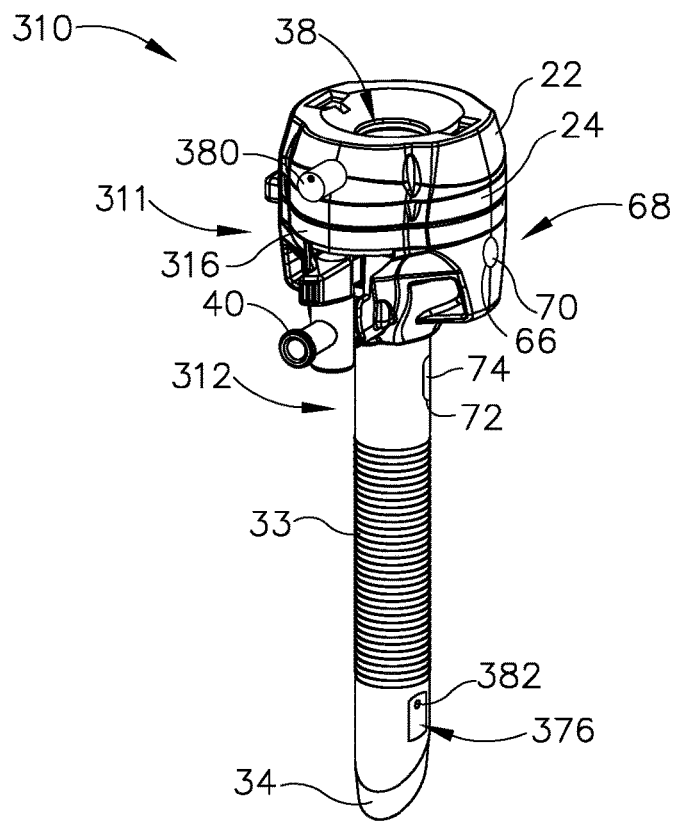
FIG. 11 depicts a perspective view of a third suturing trocar assembly having a cannula assembly with a third catch arm for releasably capturing a suture thread.

C. Third Suturing Trocar Assembly with a Third Deployable Catch Arm Repositioned within a Patient Via Rotation of Trocar Assembly FIGS. 11-12B illustrate a third exemplary suturing trocar assembly (310) with a cannula assembly (311) having a cannula (312) and obturator (14). With respect to FIG. 11, cannula assembly (311) has a distal end portion with cannula sidewall (33) distally extending to beveled end (34). In addition, the distal end portion of cannula assembly (311) includes a catch arm (376) positioned in cannula sidewall (33) that is selectively movable from a retracted position to a deployed position. In the retracted position, catch arm (376) with the remainder of the distal end portion of cannula sidewall (33) is positioned relatively radially inward and thus configured to be inserted into the patient and removed from the patient. In the deployed position, catch arm (376) extends relatively radially outward to align with channel (68) for receiving needle (490) (see FIG. 15A) thereagainst. Catch arm (376) in the deployed position, such as a catch deployed position, is thereby configured to releasably capture suture thread (492) (see FIG. 15A) for suturing tissue (17) (see FIG. 15A). Once captured, cannula assembly (311) is rotated 180 degrees relative to the patient such that catch arm (176) is in a release deployed position for reattaching suture thread (492) (see FIG. 15A) to needle (490) (see FIG. 15A) to be withdrawn via another channel (68) through tissue (17) (see FIG. 15A) as generally discussed below in use with respect to FIGS. 15A-15D.

Figure 12A:
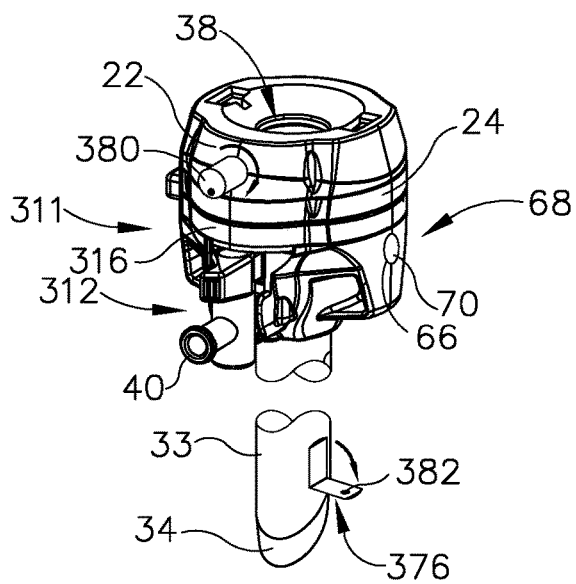
FIG. 12A depicts a perspective view of the suturing trocar assembly of FIG. 11 with the catch arm in a deployed position.
Figure 12B:
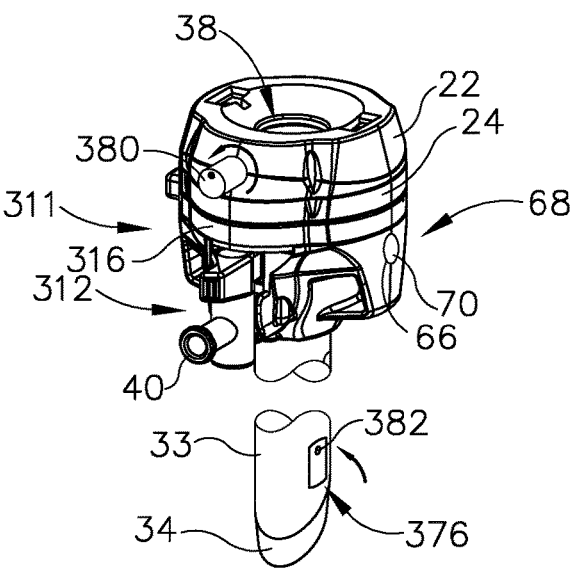
FIG. 12B depicts the perspective view of the suturing trocar assembly similar to FIG. 12A, but with the catch arm in a retracted position.

FIGS. 12A and 12B show catch arm (376) in the deployed and retracted positions, respectively. A trocar housing (316) includes an actuator (380) operatively connected to catch arm (376) and configured to direct movement of catch arm (376). Actuator (380) in the unactuated position (see FIG. 11) causes catch arm (376) to remain in the retracted position. In the present example, cannula sidewall (33) has an outer surface that defines the generally circular profile that is transverse to the longitudinal axis along which cannula (312) extends. Catch arm (376) in the retracted position is generally parallel with the longitudinal axis and within this transverse circular profile in order to inhibit catch arm (376) from engaging, or evening catching, on tissue (17) (see FIG. 15A) upon insertion.

Selectively manipulating actuator (380) in a clockwise direction causes catch arm (376) to proximally pivot to the deployed position shown in FIG. 12A. In the deployed position, catch arm (376) extends radially outward from cannula sidewall (33). More particularly, in the present example, catch arm (376) extends transversely relative to the longitudinal axis and radially outward to align with channel (68). Catch arm (376) further includes a catch hole (382) that extends transversely therethrough and aligns with channel (68) so that needle (490) (see FIG. 15A) may be simultaneously received within channel (68) and catch hole (382) in use. Catch arm (376) is configured to releasably capture suture thread (492) (see FIG. 15A) within catch hole (382) for suturing tissue (17) (see FIG. 15A) as described below in greater detail.

D. Fourth Suturing Trocar Assembly with a Fourth Deployable Catch Arm Repositioned within a Patient Via Rotation of Trocar Assembly FIGS. 13A-14C illustrate a fourth exemplary suturing trocar assembly (410) with a cannula assembly (411), which has a cannula (412), and an obturator (414) that operate similar to those discussed above with respective features for performing a surgical procedure. Suturing trocar assembly (410) also includes a pair of openings (466, 472) with respective seals (470, 474) and a channel (468) for suturing tissue (17) (see FIG. 15A) without removing suturing trocar assembly (410) from the patient. With respect to FIG. 13A, obturator (414) has a distal end portion with a shaft (448) distally extending to a tip (420). In addition, the distal end portion of obturator (414) includes a catch arm (476) that is selectively movable from a retracted position to a deployed position. In the retracted position, catch arm (476) with the remainder of the distal end portion of obturator (414) is positioned relatively radially inward and thus configured to be inserted into the patient and removed from the patient, such as via cannula (412). In the deployed position, catch arm (476) extends relatively radially outward to align with channel (468) for receiving needle (492) (see FIG. 15A) thereagainst. Catch arm (476) in the deployed position, such as a catch deployed position, is thereby configured to releasably capture suture thread (492) (see FIG. 15A) for suturing tissue (17) (see FIG. 15A). Once captured, cannula assembly (411) is rotated 180 degrees relative to the patient such that catch arm (476) is in a release deployed position for reattaching suture thread (492) (see FIG. 15A) to needle (492) (see FIG. 15A) to be withdrawn via channel (468) through tissue (17) (see FIG. 15A) as generally discussed below in use with respect to FIGS. 15A-15D.

While suturing trocar assembly (410) has similar features to those discussed herein, at least one difference of a proximal end portion of suturing trocar assembly (410) is a rotatably movable interface between a handle head (446) of obturator (414) and a trocar housing (416). To this end, FIGS. 13A and 14A illustrate handle head (446) with a plurality of radially inward extending tabs (484) received respectively within a plurality of spiral slots (486). Spiral slots (486) longitudinally extend and angularly spiral about trocar housing (416) and are configured to movably receive respective tabs (484) therein. Tabs (484) within spiral slots (486) cooperate similar to a threaded engagement such that rotating obturator (414) counterclockwise causes obturator (414) to also distally move relative to cannula assembly (411) as shown in FIGS. 13B and 14B. Such distal movement causes catch arm (476), to distally extend from a distal end (434) of a cannula sidewall (434) for deployment. Otherwise, in the present example, cannula sidewall (433) prevents deployment of catch arm (476) prior to such distal extension.

FIGS. 13B and 14B show catch arm (376) being extend from the retracted position to the deployed position, whereas FIGS. 13C and 14C show catch arm (376) being returned from the deployed position to the retracted position. Handle head (446) of obturator (414) includes an actuator (480) operatively connected to catch arm (476) via a push-pull cable (477) and configured to direct movement of catch arm (476). Actuator (480) in the unactuated position (see FIG. 14A) causes catch arm (476) to remain in the retracted position. In the present example, cannula sidewall (433) has an outer surface that defines the generally circular profile that is transverse to the longitudinal axis along which cannula (412) extends. Catch arm (476) in the retracted position is generally parallel with the longitudinal axis and within this transverse circular profile in order to inhibit catch arm (476) from engaging, or even catching, on tissue (17) (see FIG. 15A) upon insertion.

Selectively manipulating actuator (480) in a distal direction causes catch arm (476) to distally pivot to the deployed position. In the deployed position, catch arm (476) extends radially outward from shaft (448). More particularly, in the present example, catch arm (476) extends transversely relative to the longitudinal axis and radially outward to align with channel (468). Catch arm (476) further includes a catch hole (482) that extends transversely therethrough and aligns with channel (468) so that needle (490) (see FIG. 15A) may be simultaneously received within channel (468) and catch hole (482) in use. Catch arm (476) is configured to releasably capture suture thread (492) (see FIG. 15A) within catch hole (482) for suturing tissue (17) (see FIG. 15A).

E. Method of Suturing a Tissue with a Deployable Catch Arm and Suture Thread

In use, as shown in FIGS. 15A-15D, a needle (490) and a suture thread (492) in conjunction with suturing trocar assembly (410) are configured to suture tissue (17). With suturing trocar assembly (410) positioned within tissue opening (58) and catch arm (476) in the catch deployed position, clinician inserts needle (490) through channel (468) along the suture path with a distal suture thread end (494) removably attached to a distal needle end (496). Distally along the suture path from opening (472), distal needle end (496) and distal suture thread end (494) pass through fascia (56) on one side of tissue opening (58). Continuing distally along the suture path from fascia (56), distal needle end (496) and distal suture thread end (494) are received within catch hole (482) of catch arm (476). Clinician manipulates needle (490) such that distal suture thread end (494) attaches to catch arm (476), but releases from distal needle end (496). Once detached from suture thread (492), clinician withdraws needle (490) from fascia (56) and channel (468), but suture thread (492) remains within fascia (56) on the one side of tissue opening (58) as shown in FIG. 15B.

FIG. 15C shows clinician manipulating suturing trocar assembly (410) to move catch arm (476) from the catch deployed position to the release deployed position a predetermined distance for repositioning distal suture thread end (494) to the other, opposing side of tissue opening (58). More particularly, in the present example, clinician rotates an entirety of suturing trocar assembly (410) with catch arm (476) extended to the deployed position such that catch arm (467) similarly rotates from the catch deployed position to the release deployed position. Distal suture thread end (494) remains attached to catch arm (476) throughout this movement and is thereby repositioned relative to tissue (17) for continued suturing.

With respect to FIG. 15D, clinician again inserts needle (490) through channel (468) along the suture path through fascia (56), but on the opposing side of tissue opening (58). Distal needle end (496) is received within catch hole (482) in the release deployed position and reattaches to distal suture thread end (494) as distal suture thread end (494) is also released from catch arm (476). Once distal needle end (496) is reattached to distal suture thread end (494), clinician proximally withdraws needle (490) and suture thread (492) such that distal suture thread end (494) is inserted and withdrawn through fascia (56) as shown in FIGS. 15E-15F. Needle (490) followed by suturing trocar assembly (410) are then removed by clinician such that suture thread (492) forms a loop through fascia (56) on opposing sides of tissue opening (58). As shown in FIG. 15D, clinician tightens and ties suture thread (492) to suture close tissue opening (58) at fascia (56). Additional suturing may be performed by the clinician as desired to further close tissue opening (58).

The above method of suturing tissue opening (58) closed with suturing trocar assembly (410) may be similarly performed with other suturing trocar assemblies (110, 210, 310) described above. It will be appreciated that similarly described features performed similar functions to that shown and described with respect to FIGS. 15A-15D. In contrast, it will be further appreciated that various distinguishing features operate as discussed above for each respective suturing trocar assembly (110, 210, 310), particularly with respect to transitioning catch arms (176, 276, 376) from catch deployed positions to release deployed positions. The invention is thus not intended to be unnecessarily limited to use with suturing trocar assembly (410).

III. Barbed Suture Thread and Related Methods of Suturing Tissue

While suture thread (492) is knotted to effectively secure suture thread (492) and close tissue opening (58), it may be beneficial in some instances for suture thread (492) to include a securement to affix one portion of suture thread (492) relative to another portion of suture thread (492) without knotting. FIGS. 16-19C shows a unidirectional barbed suture thread (510) with such a securement in the form of a plurality of barbs (512) extending along a thread body (514) to a pledget end (516). For purposes of reference with respect to suture thread (510), pledget end (516) is at a distal end of thread body (514) with the opposing end being a proximal end. Each barb (512) extends longitudinally and radially outward in a direction toward pledget end (516) such that barbs (512) are at an oblique angle relative to thread body (514). Barbs (512) are configured to be proximally inserted into tissue (17) (see FIG. 19A) such that barbs (512) are inhibited from catching tissue (17). In contrast, barbs (512) are configured to grip tissue in the distal direction to inhibit unidirectional barbed suture thread (510) from backing out in the distal direction. Additionally, pledget end (516) is configured to catch tissue (17) (see FIG. 19A) in a direction opposite to that of barbs (512) to thereby secure unidirectional barbed suture thread (510) in tissue (17) (see FIG. 19A).

Figure 16:
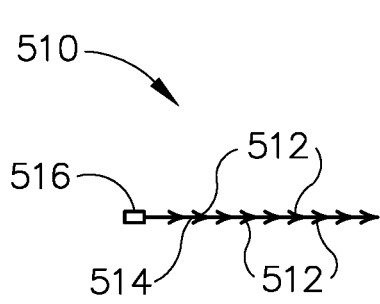
FIG. 16 depicts a side elevational view of a unidirectional barbed suture thread.
Figure 17:
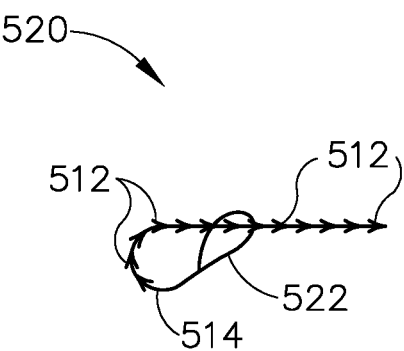
FIG. 17 depicts a side elevational view of an alternative unidirectional barbed suture thread.

FIG. 17 shows an alternative unidirectional barbed suture (520) similar to unidirectional barb suture (510) (see FIG. 16), but having a looped end (522) rather than pledget end (516) (see FIG. 16). Upon insertion through tissue (17) (see FIG. 19A), clinician inserts the proximal end portion of unidirectional barbed suture (520) through distal looped end (522) for noosing unidirectional barbed suture (520) tight and closing tissue opening (58) (see FIG. 19A). Barbs (512) thereby catch on looped end (522) when tightened to inhibit loosening of unidirectional barbed suture (520) similar to a ratchet mechanism.

Figure 18:
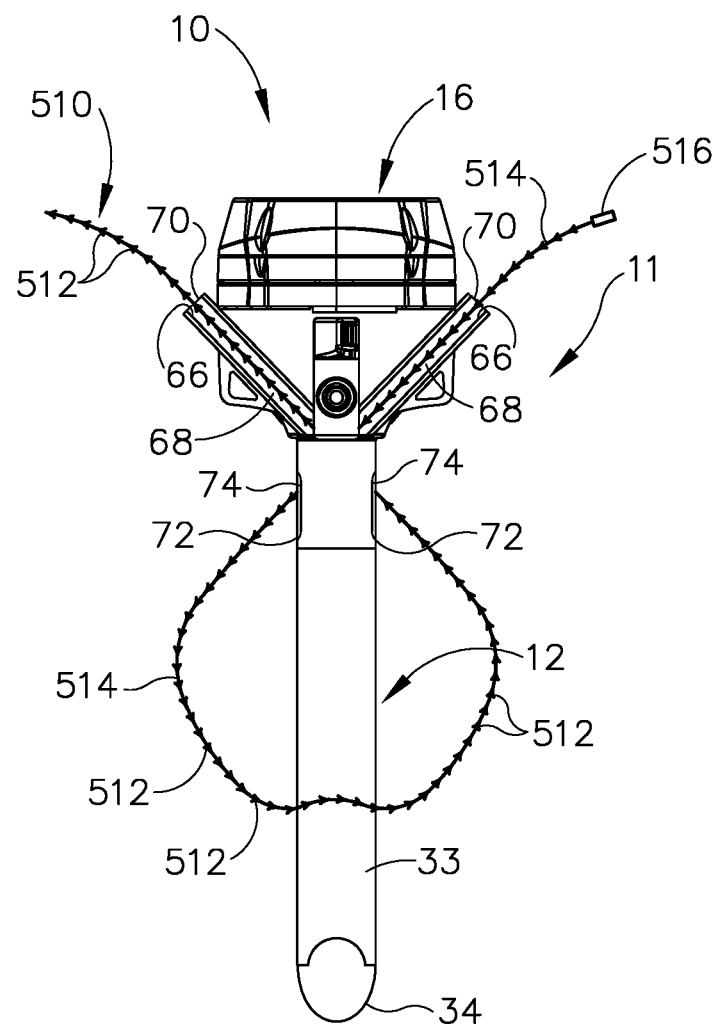
FIG. 18 depicts a side elevational view of the trocar assembly of FIG. 1 with the unidirectional barbed suture thread of FIG. 16 having various components removed for clarity.
Figure 20:
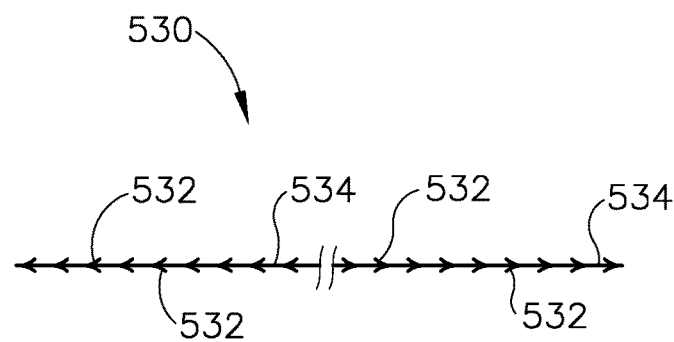
FIG. 20 depicts a side elevational view of a bidirectional barbed suture thread.
Figure 21A:
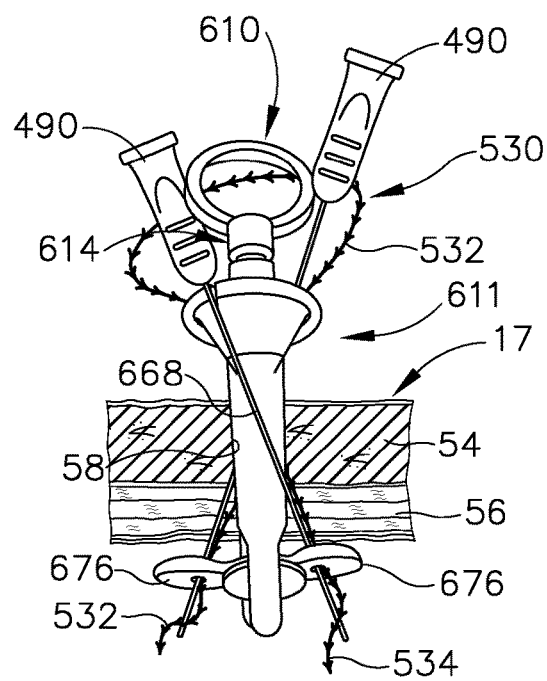
FIG. 21A depicts a perspective sectional view of a yet another exemplary suturing trocar assembly inserted into a tissue with the bidirectional barbed suture thread of FIG. 20.
Figure 21B:
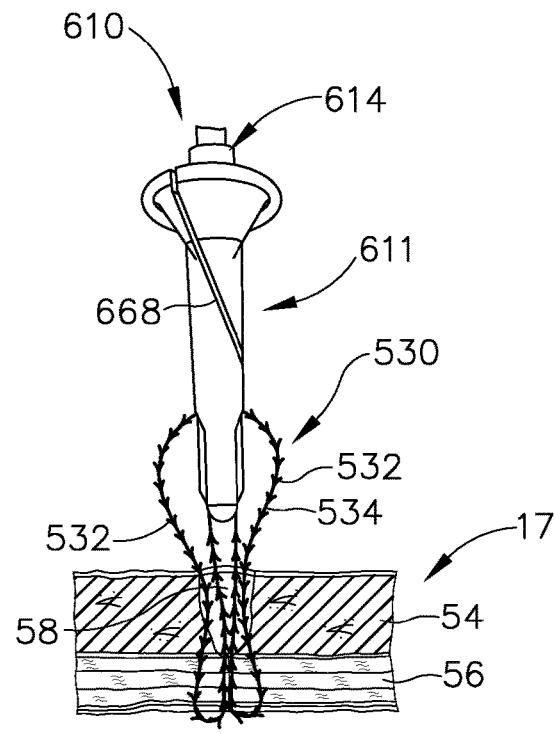
FIG. 21B depicts the perspective sectional view of the suturing trocar assembly similar to FIG. 21A, but with the suturing trocar assembly being removed from the tissue.

In use, FIG. 18-19C show unidirectional barbed suture (510) following the suture path through channels (68) of trocar assembly (10) as discussed herein, although alternative suturing trocar assemblies may be similarly used. As briefly discussed above, unidirectional barbed suture (510) is proximally inserted through fascia (56) on opposing sides of tissue opening (58) as shown in FIG. 19A. Clinician pulls on proximal end portion of thread body (514) out from tissue opening (58) to similarly pull pledget end (516) into tissue opening (58) to catch on fascia (56). Further pulling on the proximal end portion of thread body (514) tightens unidirectional barbed suture (510) as shown in FIGS. 19B-19C and closes tissue opening (58) between barbs (512) and pledget end (516).

FIGS. 22A-22C show a bidirectional barbed suture (530) for an alternative suture path of an alternative trocar assembly (610) having a cannula assembly (611), an obturator (614), and a pair of opposing catch arms (676). Bidirectional barbed suture (530) has a first plurality of barbs (532) extending longitudinally and radially outward and in a first direction from a thread body (534). In addition, bidirectional barbed suture (530) also has a second plurality of barbs (532) extending longitudinally and radially outward and in a second direction from thread body (534) opposite from first direction. End portions of thread body (534) are each inserted through respective channels (668) and inserted into fascia (56) as shown in FIGS. 21A-22A. End portions of thread body (534) are then pulled out from tissue opening (58) to be looped and tightened as shown in FIGS. 22B-22C such that barbs (532) catch tissue (17) and other looped barbs (532) to suture tissue opening (58) closed.

IV. Pledget Surgical Instrument for Suturing Tissue

Figure 23:
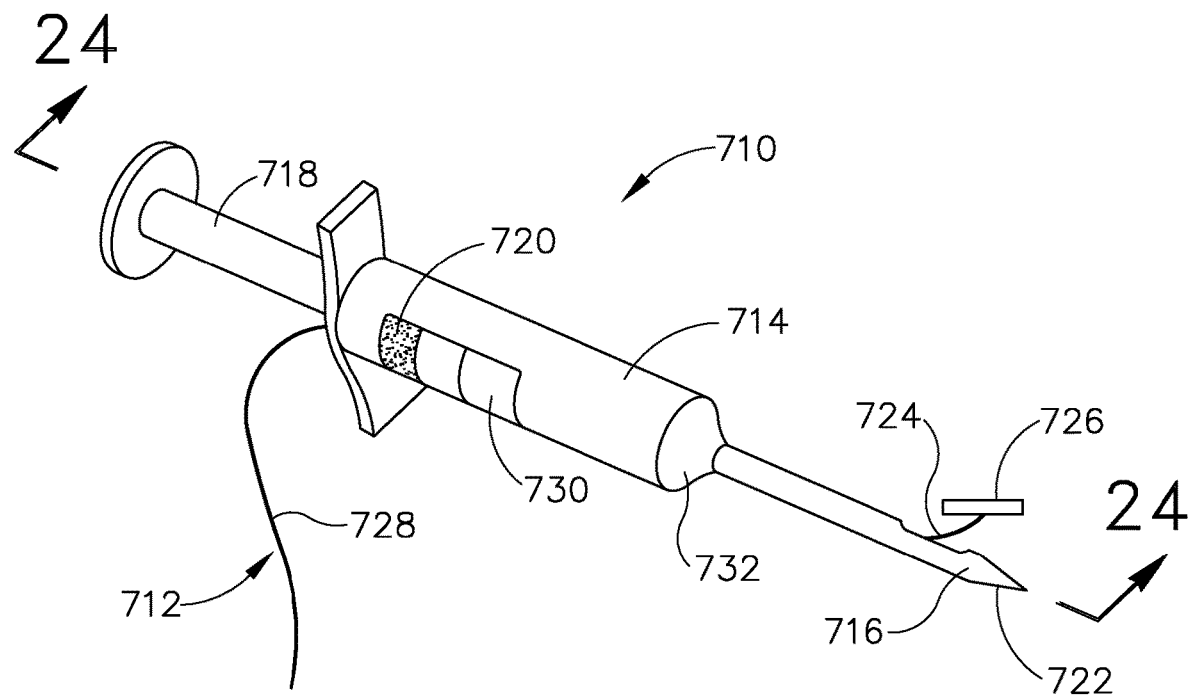
FIG. 23 depicts a perspective view of a suturing surgical instrument with a slip pledget suture thread.
Figure 24:
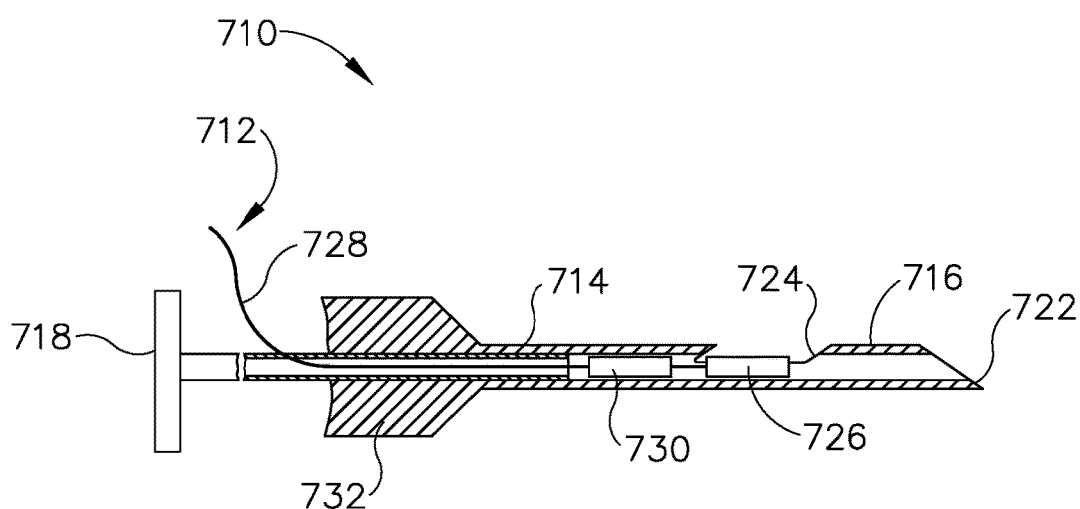
FIG. 24 depicts an enlarged cross-sectional view of the suturing surgical instrument of FIG. 23 taken along section line 24-24 of FIG. 23.

FIGS. 23-24 show a pledget surgical instrument (710) configured to position a slip pledget suture thread (712) into tissue (17) (see FIG. 28A) for suturing tissue (17) (see FIG. 28A). Pledget surgical instrument (710) includes a barrel body (714) with a distally extending needle introducer (716) as well as a plunger (718) slidably received within barrel body (714). Barrel body (714) is configured to receive slip pledget suture thread (712) for being inserted into tissue (17) (see FIG. 28A) via needle introducer (716). Barrel body (714) of the present example also includes a window (720) for viewing slip pledget suture thread (712) within barrel body (714). Needle introducer (716) has a distal beveled end (722) configured to penetrate tissue (17) (see FIG. 28A) and a discharge slot (724) extending longitudinally through a sidewall of needle introducer (716) between beveled end (722) and barrel body (714). Slip pledget suture thread (712) is configured to be ejected from discharge slot (724) for positioning slip pledget suture thread (712) in tissue (17) (see FIG. 28A) as discussed below in greater detail.

Plunger (718) is configured to be selectively translated by the clinician into barrel body (714) and against slip pledget suture thread (712) contained therein. Thereby, plunger (718) urges a distal pledget end (726) from discharge slot (724) followed by at least a portion of thread body (728). Further selective translation of plunger (718) into barrel body (714) urges a proximal pledget end (728) from discharge slot (724) followed by a remaining portion of thread boy (728). In one example, pledget surgical instrument (710) also includes a plug body (732) between barrel body (714) and needle introducer (716) that is configured to at least partially plug tissue opening (58) (see FIG. 28A) in use to inhibit fluid, such as insufflation fluid, from tissue opening (58) (see FIG. 28A).

FIG. 25-26B show slip pledget suture thread (712) having thread body (728) as well as distal and proximal pledget ends (726, 730). FIGS. 26A-26B respectively show distal pledget end (726) and a distal portion of thread body (728) looped around a proximal portion of thread body (728) with proximal pledget (730) slidably connected on thread body (728) therebetween. Selectively pulling on thread body (728) thereby nooses slip pledget suture thread (712) tighter.

An alternative barbed pledget suture thread (740) is shown in FIGS. 27A-27B. Barbed pledget suture thread (740) include a distal end pledget (742) connected to a thread body (744) as well as a slidable proximal end pledget (746). Rather than looping thread body (744) as discussed above with respect to thread body (728) (see FIG. 26A), barbed pledget suture thread (740) further includes a plurality of barbs (748) configured to allow distal translation of proximal end pledget (746) toward distal end pledget (742), but inhibit proximal translation of proximal end pledget (746) away from distal end pledget (742). In other words, proximal end pledget (746) and barbs (748) cooperate similar to a ratchet mechanism for securing tightened barbed pledget suture thread (740) in tissue (17) (see FIG. 28A) for closing tissue opening (58) (see FIG. 28A).

Figure 28D:
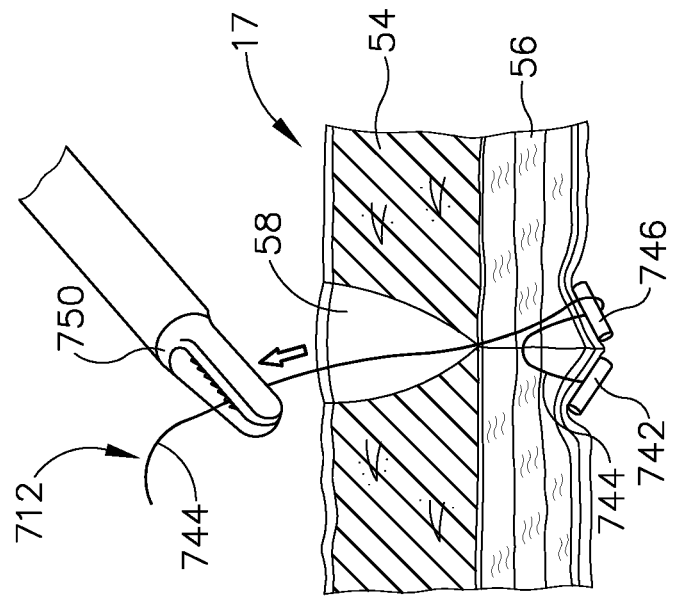
FIG. 28D depicts the perspective sectional view of the suturing surgical instrument and the slip pledget suture thread similar to FIG. 28C, but with the suturing surgical instrument removed from the tissue opening and a clamp jaw tightening the slip pledget suture thread to the looped closed configuration for closing the tissue opening.

In use, with respect to FIGS. 28A-28D, pledget surgical instrument (710) contains slip pledget suture thread (712) and needle introducer (716) is inserted into fascia (56) on one side of tissue opening (58). More particularly, needle introducer (716) is distally inserted such that discharge slot (724) also slides through and distal of fascia (56) within the patient as shown in FIG. 28A. The clinician then selectively distally translates plunger (718) to urge distal pledget end (726) from discharge slot (724) and position distal pledget end (726) in fascia (56). Pledget surgical instrument (710) is further manipulated such that needle introducer (716) is again inserted into fascia (56) on another, opposing side of tissue opening (58) as shown in FIG. 28B. The clinician then again selectively distally translates plunger (718) to urge proximal pledget end (730) from discharge slot (724) and position proximal pledget end (730) in fascia (56).

Figure 28C:
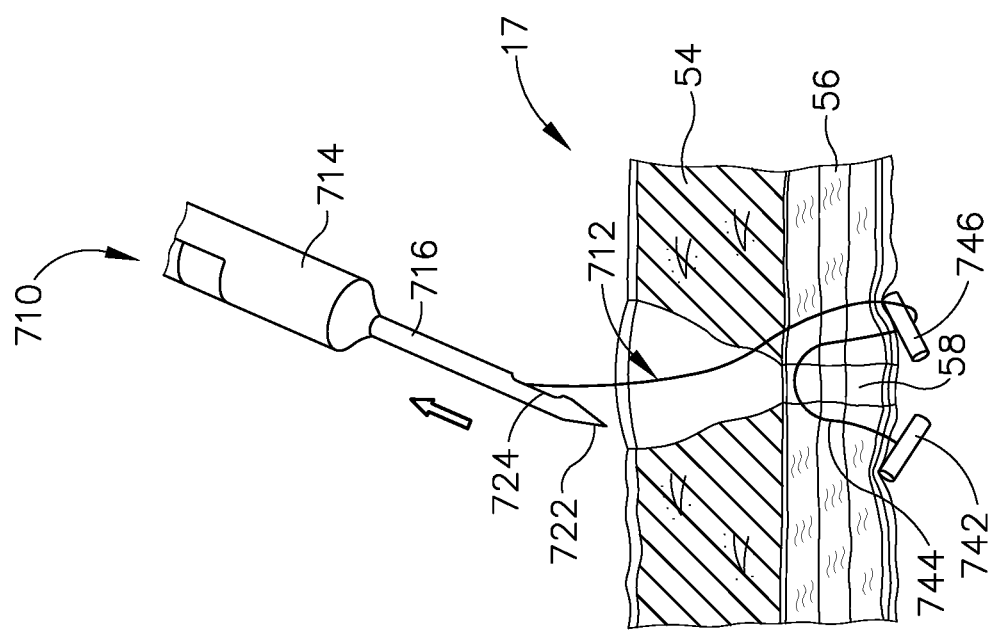
FIG. 28C depicts the perspective sectional view of the suturing surgical instrument and the slip pledget suture thread similar to FIG. 28B, but with the suturing surgical instrument being removed from the tissue opening.

FIGS. 28C-28D show pledget surgical instrument (710) being withdrawn from tissue opening (58) and the remainder of thread body (728) being pulled from within surgical instrument (710). In the present example, thread body (728) is looped as discussed above. A clamp jaw (750) is then manipulated by clinician in order to grip and pull the remainder of thread body (728) to tighten pledget suture thread (712) for closing tissue opening (58).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A trocar assembly, comprising: (a) a cannula assembly, including: (i) a housing having a proximal opening, (ii) a cannula extending distally from the trocar housing to a distal opening, and (iii) a working channel defining a longitudinal axis and extending from the proximal opening to the distal opening; (b) an obturator assembly, including: (i) a proximal head, (ii) a distal tip configured to penetrate tissue of a patient, and (iii) a shaft extending from the proximal head to the distal tip and configured to be received within the working channel of the cannula assembly such that the distal tip projects distally beyond the distal opening of the cannula; and (c) a catch arm selectively moveable from a retracted position to a first deployed position and a second deployed position and configured to releasably capture a suture thread from a needle, wherein the catch arm in the retracted position is positioned radially inward from the first deployed position for insertion into the patient, wherein the catch arm in the first deployed position is positioned radially outward from the retracted position for releasably capturing the suture thread, and wherein the catch arm is configured to be moved a predetermined distance from the first deployed position to the second deployed position and release the captured suture thread from the second deployed position for suturing the tissue.

Example 2

The trocar assembly of Example 1, wherein the cannula assembly further includes a needle channel extending across the longitudinal axis and configured to receive a needle with a suture thread for suturing a tissue of a patient, and wherein catch arm in the first deployed position linearly aligns with the needle channel to receive the suture thread therefrom.

Example 3

The trocar assembly of Example 2, wherein the catch arm includes a catch hole configured to align with the needle channel in the first deployed position and thereby receive the needle and releasably capture the suture thread therein.

Example 4

The trocar assembly of any one or more of Examples 1 through 3, wherein the cannula defines an outer transverse profile, wherein the catch arm is generally within the outer transverse profile in the retracted position, and wherein the catch arm extends radially outward from the outer transverse profile in the deployed position.

Example 5

The trocar assembly of any one or more of Examples 1 through 4, wherein the catch arm in the retracted position is generally parallel with the longitudinal axis, and wherein the catch arm in the first deployed position is generally transverse to the longitudinal axis.

Example 6

The trocar assembly of any one or more of Examples 1 through 5, wherein the catch arm is configured to pivot from the retracted position to the first deployed position.

Example 7

The trocar assembly of any one or more of Examples 1 through 6, wherein the first deployed position is angularly opposite from the second deployed position about the longitudinal axis.

Example 8

The trocar assembly of any one or more of Examples 1 through 7, wherein the catch arm in the first deployed position is secured relative to the shaft of the obturator assembly such that the catch arm is configured to rotate to the second deployed position relative to the cannula of the trocar assembly in response to rotation of the shaft of the obturator assembly.

Example 9

The trocar assembly of Example 8, wherein the catch arm is pivotally connected to the shaft of the obturator assembly.

Example 10

The trocar assembly of any one or more of Examples 1 through 9, wherein the catch arm in the first deployed position is secured relative to the shaft of the obturator assembly in a first transverse direction, wherein the catch arm in the second deployed position is secured relative to the shaft of the obturator assembly in a second transverse direction, and wherein the first and second directions are respectively associated with opposing sides of the shaft of the obturator assembly.

Example 11

The trocar assembly of Example 10, wherein the catch arm is configured to pivot from the first deployed position to the second deployed position through the retracted position.

Example 12

The trocar assembly of Example 11, wherein the catch arm is pivotally connected to the shaft of the obturator assembly.

Example 13

The trocar assembly of any one or more of Examples 1 through 12, wherein the catch arm in the first deployed position is secured relative to the cannula such that rotating the cannula is configured to rotate the catch arm to the second deployed position.

Example 14

The trocar assembly of Example 13, wherein the catch arm is pivotally connected to the cannula of the trocar assembly.

Example 15

The trocar assembly of any one or more of Examples 1 through 14, further comprising an actuator operatively connected to the catch arm, wherein the actuator is configured to be selectively manipulated to thereby selectively move the catch arm from the retracted position to the first deployed position.

Example 16

An obturator assembly, comprising: (a) a proximal end portion; (b) a distal end portion having a distal tip configured to penetrate tissue of a patient; (c) a shaft extending longitudinally between the proximal end portion and the distal end portion; and (d) a catch arm connected to the distal end portion and selectively moveable from a retracted position to a deployed position and configured to releasably capture a suture thread from a needle, wherein the catch arm in the retracted position is positioned radially inward from the deployed position for insertion into the patient, and wherein the catch arm in the deployed position is positioned radially outward from the retracted position for releasably capturing the suture thread.

Example 17

A method of suturing a tissue opening with a suture thread and a trocar assembly, wherein the trocar assembly includes a cannula assembly, an obturator assembly, and a catch arm, wherein the catch arm is selectively moveable from a retracted position to a first deployed position and configured to releasably capture the suture thread from a needle, wherein the catch arm in the retracted position is positioned radially inward from the first deployed position for insertion into the patient, and wherein the catch arm in the first deployed position is positioned radially outward from the retracted position for releasably capturing the suture thread. the method including: (a) penetrating the tissue with the trocar assembly and positioning the catch arm within the patient while the catch arm is in the retracted position; (b) extending the catch arm radially outwardly to first deployed position; (c) inserting a thread end portion of the suture thread into the tissue with the needle; (d) releasably capturing the thread end portion of the suture thread with the catch arm; (e) moving the catch arm to a second deployed position with the thread end portion of the suture thread releasably captured thereto; (f) releasing the thread end portion of the suture thread from the catch arm; and (g) withdrawing the thread end portion of the suture thread from the patient to thereby suture the tissue opening.

Example 18

The method Example 17, wherein moving the catch arm further includes rotating the obturator assembly relative to the cannula assembly.

Example 19

The method any one or more of Examples 17 through 18, wherein moving the catch arm further includes rotating the cannula assembly relative to the patient.

Example 20

The method of any one or more of Examples 17 through 19, wherein moving the catch arm further includes pivoting the catch arm from the first deployed position to the second deployed position through the retracted position.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

The teachings presented herein may be further combined with various teachings of any one or more of the following: U.S. application Ser. No. 15/637,702, entitled "Suture Grasping Instrument," filed on Jun. 29, 2017, published as U.S. Pub. No. 2019/0000440 on Jan. 3, 2019, the disclosure of which is incorporated by reference herein; U.S. application Ser. No. 15/637,683, filed on Jun. 29, 2017, published as U.S. Pub. No. 2019/0000505 on Jan. 3, 2019, incorporated by reference above, U.S. App. No. 15/637,688, issued as U.S. Pat. No. 10/485,580 on Nov. 26, 2019, incorporated by reference above; U.S. application Ser. No. 15/637,712, entitled "Suture Passing Instrument with Puncture Site Identification Feature, " filed on Jun. 29, 2017, published as U.S. Pub. No. 2019/0000444 on Jan. 3, 2019, the disclosure of which is incorporated by reference herein; U.S. application No. 15/637,696, entitled "Trocar Obturator with Transverse Needle Ports," filed on Jun. 29, 2017, published s U.S. Pub. No. 2019/0000506 on Jan. 3, 2019, the disclosure of which is incorporated by reference herein; U.S. application Ser. No. 15/637,707, entitled "Surgical Port with Wound Closure Channels," filed on filed on Jun. 29, 2017, issued as U.S. Pat. No. 10,568,619 on Feb. 25, 2020, the disclosure of which is incorporated by reference herein; U.S. application Ser. No. 15/637,735, entitled "Trocar Obturator with Detachable Rotary Tissue Fastener," filed on Jun. 29, 2017, published as U.S. Pub. No. 2019/0000502 on Jan. 3, 2019, the disclosure of which is incorporated by reference herein; U.S. application Ser. No. 15/637,778, entitled "Method of Suturing a Trocar Patch Incision," filed on Jun. 29, 2017, published as U.S. Pub. No. 2019/0000496 on Jan. 3, 2019, the disclosure of which is incorporated by reference herein; and/or other patents and patent application publications incorporated by reference above.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A trocar assembly, comprising:
(a) a cannula assembly, including:
(i) a housing having a proximal opening,
(ii) a cannula extending distally from the housing to a distal opening, and
(iii) a working channel defining a longitudinal axis and extending from the proximal opening to the distal opening;
(b) an obturator assembly, including:
(i) a proximal head,
(ii) a distal tip configured to penetrate a tissue of a patient,
(iii) a shaft extending from the proximal head to the distal tip and configured to be received within the working channel of the cannula assembly such that the distal tip projects distally beyond the distal opening of the cannula, and
(iv) a catch arm selectively moveable from a retracted position to a first deployed position and a second deployed position and configured to releasably capture a suture thread from a needle, wherein the catch arm in the retracted position is positioned radially inward from the first deployed position for insertion into the patient, wherein the catch arm in the first deployed position is positioned radially outward from the retracted position for releasably capturing the suture thread, and wherein the catch arm is configured to be moved a predetermined distance from the first deployed position to the second deployed position and release the captured suture thread from the second deployed position for suturing the tissue; and
(c) an actuator coupled to the proximal head and operatively connected to the catch arm, wherein the actuator is selectively moveable between an active position and an inactive position, wherein the actuator is selectively movable in the active position to thereby actuate the catch arm relative to the shaft between the retracted position, the first deployed position, and the second deployed position.

2. The trocar assembly of claim 1, wherein the cannula assembly further includes a needle channel extending across the longitudinal axis and configured to receive the needle with the suture thread for suturing the tissue of the patient, and wherein catch arm in the first deployed position linearly aligns with the needle channel to receive the suture thread therefrom.

3. The trocar assembly of claim 2, wherein the catch arm includes a catch hole configured to align with the needle channel in the first deployed position and thereby receive the needle and releasably capture the suture thread therein.

4. The trocar assembly of claim 1, wherein the cannula defines an outer transverse profile, wherein the catch arm is generally within the outer transverse profile in the retracted position, and wherein the catch arm extends radially outward from the outer transverse profile in the first deployed position and the second deployed position.

5. The trocar assembly of claim 1, wherein the catch arm in the retracted position is generally parallel with the longitudinal axis, and wherein the catch arm in the first deployed position is generally transverse to the longitudinal axis.

6. The trocar assembly of claim 1, wherein the catch arm is configured to pivot from the retracted position to the first deployed position.

7. The trocar assembly of claim 1, wherein the first deployed position is angularly opposite from the second deployed position about the longitudinal axis.

8. The trocar assembly of claim 1, wherein the catch arm in the first deployed position is secured relative to the shaft of the obturator assembly such that the catch arm is configured to rotate to the second deployed position relative to the cannula of the trocar assembly in response to rotation of the shaft of the obturator assembly.

9. The trocar assembly of claim 1, wherein the catch arm is pivotally connected to the shaft of the obturator assembly.

10. The trocar assembly of claim 1, wherein the catch arm in the first deployed position is secured relative to the shaft of the obturator assembly in a first transverse direction, wherein the catch arm in the second deployed position is secured relative to the shaft of the obturator assembly in a second transverse direction, and wherein the first and second directions are respectively associated with opposing sides of the shaft of the obturator assembly.

11. The trocar assembly of claim 10, wherein the catch arm is configured to pivot from the first deployed position to the second deployed position through the retracted position.

12. The trocar assembly of claim 11, wherein the catch arm is pivotally connected to the shaft of the obturator assembly.

13. The trocar assembly of claim 1, wherein the actuator is configured to translate between the inactive position and the active position, wherein the actuator is configured to rotate in the active position to thereby actuate the catch arm.

14. The trocar assembly of claim 1, wherein the actuator in the inactive position is recessed distally within the proximal head, wherein the actuator in the active position protrudes proximally from the proximal head.

15. The trocar assembly of claim 1, wherein the catch arm is pivotable about a pivot axis that extends transversely to the longitudinal axis, wherein the actuator in the active position is selectively rotatable about the longitudinal axis to actuate the catch arm about the pivot axis between the retracted position, the first deployed position, and the second deployed position.

16. A trocar assembly, comprising:
(a) a cannula assembly, including:
(i) a housing having a proximal opening,
(ii) a cannula extending distally from the housing to a distal opening, and
(iii) a working channel defining a longitudinal axis and extending from the proximal opening to the distal opening; and
(b) an obturator assembly, including:
(i) a proximal head,
(ii) a distal tip configured to penetrate a tissue of a patient,
(iii) a shaft extending from the proximal head to a distal end portion having a distal tip and configured to be received within the working channel of the cannula assembly such that the distal tip projects distally beyond the distal opening of the cannula, wherein the distal end portion includes a forked portion having a slot, and
(iv) a catch arm pivotably mounted within the slot, wherein the catch arm is selectively moveable from a retracted position to a first deployed position and a second deployed position and configured to releasably capture a suture thread from a needle, wherein the catch arm in the retracted position is positioned radially inward from the first deployed position for insertion into the patient, wherein the catch arm in the first deployed position is positioned radially outward from the retracted position for releasably capturing the suture thread, and wherein the catch arm is configured to release the captured suture thread from the second deployed position for suturing the tissue.

17. The trocar assembly of claim 16, wherein the cannula includes a clearance channel, wherein the clearance channel is configured to receive the catch arm in the first deployed position.

18. The trocar assembly of claim 16, wherein the cannula defines an outer transverse profile, wherein the catch arm is positioned within or in alignment with the outer transverse profile in the retracted position, and wherein the catch arm is configured to extend radially outwardly from the outer transverse profile in the first deployed position and in the second deployed position.

19. An obturator assembly configured to be inserted into a cannula assembly, the obturator assembly comprising:
(a) a head, wherein the head includes an actuator;
(b) a shaft extending distally from the head along a central axis, wherein the actuator is rotatable about the central axis; and
(c) a catch arm pivotably coupled with a distal end of the shaft and having a distal tip configured to penetrate tissue of a patient, wherein the catch arm is selectively pivotable relative to the shaft between a retracted position, a first deployed position, and a second deployed position, wherein the catch arm is configured to capture a suture thread in the first deployed position and subsequently release the suture thread in the second deployed position,
wherein the catch arm in the retracted position is configured to align coaxially with central axis,
wherein the catch arm is configured to deflect away from the central axis in a first direction toward the first deployed position in response to rotation of the actuator in a first angular direction about the central axis,
wherein the catch arm is configured to deflect away from the central axis in a second direction toward the second deployed position in response to rotation of the actuator in a second angular direction about the central axis.

20. The obturator assembly of claim 19, wherein the second direction is opposite the first direction, wherein the second angular direction is opposite the first angular direction.

* * * * *